United States Patent
Di Carlo et al.

(10) Patent No.: US 11,060,541 B2
(45) Date of Patent: Jul. 13, 2021

(54) SYSTEM AND METHOD FOR OPTICAL TRANSIENT LIQUID MOLDING OF MICROPARTICLES AND USES FOR THE SAME

(71) Applicant: THE REGENTS OF THE UNIVERSITY OF CALIFORNIA, Oakland, CA (US)

(72) Inventors: Dino Di Carlo, Los Angeles, CA (US); Chueh-Yu Wu, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 442 days.

(21) Appl. No.: 15/763,765

(22) PCT Filed: Sep. 30, 2016

(86) PCT No.: PCT/US2016/055011
§ 371 (c)(1),
(2) Date: Mar. 27, 2018

(87) PCT Pub. No.: WO2017/059367
PCT Pub. Date: Apr. 6, 2017

(65) Prior Publication Data
US 2018/0266452 A1    Sep. 20, 2018

Related U.S. Application Data
(60) Provisional application No. 62/236,782, filed on Oct. 2, 2015.

(51) Int. Cl.
*B01J 19/12* (2006.01)
*F15D 1/14* (2006.01)
(Continued)

(52) U.S. Cl.
CPC ........... *F15D 1/14* (2013.01); *B01J 19/0093* (2013.01); *B01J 19/123* (2013.01);
(Continued)

(58) Field of Classification Search
CPC ................ B01J 19/0093; B01J 19/123; B01L 3/502707; B01L 3/502761;
(Continued)

(56) References Cited

U.S. PATENT DOCUMENTS

2007/0105972 A1*  5/2007  Doyle .................. G03F 7/2012
                                                           522/1
2010/0099048 A1   4/2010  Thomas
(Continued)

FOREIGN PATENT DOCUMENTS

| KR | 10-2014-0063888 | 5/2014 |
| WO | 2010/042943 | 4/2010 |
| WO | 2013/049404 | 4/2013 |

OTHER PUBLICATIONS

PCT International Search Report for PCT/US2016/055011, Applicant: The Regents of the University of California, Form PCT/ISA/210 and 220, dated Jan. 6, 2017 (5pages).
(Continued)

*Primary Examiner* — John A McPherson
(74) *Attorney, Agent, or Firm* — Vista IP Law Group LLP

(57) ABSTRACT

A method of forming three-dimensional shaped microparticles in a microfluidic device includes flowing a mixture of a monomer and photoinitiator in a microfluidic channel having a plurality of pillars disposed therein to define a flow stream having a pre-defined shape and temporarily stopping the same. One or more portions of the flow stream are polymerized by passing polymerizing light through one or more masks and onto the flow stream, the polymerization process forming a plurality of three-dimensional shaped
(Continued)

microparticles. The three-dimensional shape of the microparticle may be geometrically complex by using non-rectangular 2D orthogonal shapes for the flow and/or masked light source. The microparticles may include protected regions on which cells can be adhered to and protected from shear forces. The flow stream is restarted to flush out the newly formed microparticles and prepare the device for the next cycle of particle formation.

16 Claims, 14 Drawing Sheets

(51) Int. Cl.
| | | |
|---|---|---|
| | *B01L 3/00* | (2006.01) |
| | *G03F 7/20* | (2006.01) |
| | *B01J 19/00* | (2006.01) |
| | *G03F 7/027* | (2006.01) |

(52) U.S. Cl.
CPC ... *B01L 3/502707* (2013.01); *B01L 3/502761* (2013.01); *B01L 3/502776* (2013.01); *G03F 7/027* (2013.01); *G03F 7/2002* (2013.01); *B01L 2200/12* (2013.01); *B01L 2400/043* (2013.01); *B01L 2400/086* (2013.01)

(58) Field of Classification Search
CPC .......... B01L 3/502776; B01L 2200/12; B01L 2400/043; B01L 2400/086; F15D 1/14; G03F 7/027; G03F 7/2002; G03F 7/028; G03F 7/031; G03F 7/2012
USPC ........................................................ 430/320
See application file for complete search history.

(56) References Cited

U.S. PATENT DOCUMENTS

| | | | |
|---|---|---|---|
| 2011/0106220 A1 | 5/2011 | DeGiorgio et al. | |
| 2011/0112603 A1 | 5/2011 | DeGiorgio et al. | |
| 2012/0326104 A1 | 12/2012 | Kwon et al. | |
| 2014/0178252 A1* | 6/2014 | Hatch ............... | B01L 3/502707 422/69 |
| 2014/0230909 A1 | 8/2014 | Di Carlo et al. | |

OTHER PUBLICATIONS

PCT Written Opinion of the International Search Authority for PCT/US2016/055011, Applicant: The Regents of the University of California, Form PCT/ISA/237, dated Jan. 6, 2017 (8pages).

Amini, Hamed et al., Engineering fluid flow using sequenced microstructures, Nature Communications, 4:1826, DOI: 10.1038/ncomms2841/ncomms2841, www.nature.com/naturecommunications, Received Sep. 5, 2012, Accepted Apr. 7, 2013, Published May 7, 2013.

Bong, Ki Wan et al., Lock release lithography for 3D and composite microparticles, Lab Chip, 2009, 9, 863-866.

Boyd, Darryl A., Design and fabrication of uniquely shaped thiol-ene microfibers using a two-stage hydrodynamic focusing design, Lab Chip, 2013, 13, 3105.

Dendukuri, Dhananjay et al., Continuous-flow lithography for high-throughput microparticle synthesis, Nature Materials, vol. 5, May 2006, www.nature.com/naturematerials.

Dendukuri, Dhananjay et al., Stop-flow lithography in a microfludic device, Lab Chip, 2007, 7, 818-828.

Nunes, Janine K. et al., Fabricating Shaped Microfibers with Inertial Microfluidics, Adv. Mater. 2014, 26, 3712-3717.

Paulsen, Kevin S. et al., Optofluidic fabrication for 3D-shaped particles, Nature Communications, 6:6976, DOI: 10.1038/ncomms7976, www.nature.com/naturecommunications, Received Nov. 14, 2014, Accepted Mar. 19, 2015, Published Apr. 23, 2015.

Thangawng, Abel L. et al., A simple sheath-flow microfluidic device for micro/nanomanufacturing: fabrication of hydrodynamically shaped polymer fibers, Lab Chip, 2009, 9, 3126-3130.

Uspal, William E. et al., Engineering particle trajectories in microfluidic flows using particle shape, Nature Communications, 4:2666, DOI: 10.1038/ncomms3666, www.nature.com/naturecommunications, Received Apr. 25, 2013, Accepted Sep. 25, 2013, Published Nov. 1, 2013.

Wu, Chueh-Yu et al., Rapid Software-Based Design and Optical Transient Liquid Molding of Microparticles, Adv. Mater. 2015, 27, 7970-7978.

Di Carlo Laboratory Microfluidic Biotechnology, UCLA Software, uFlow, A computer-aided design (CAD) tool for the rational design of inertial flows, http://www.biomicrofluidics.com/software.php (7pages).

PCT International Preliminary Report on Patentability (Chapter I of the Patent Cooperation Treaty) for PCT/US2016/055011, Applicant: The Regents of the University of California, Form PCT/IB/326 and 373, dated Apr. 12, 2018 (10pages).

\* cited by examiner

SYSTEM AND METHOD FOR OPTICAL TRANSIENT LIQUID MOLDING OF MICROPARTICLES AND USES FOR THE SAME

RELATED APPLICATION

This Application is a U.S. National Stage filing under 35 U.S.C. § 371 of International Application No. PCT/US2016/055011, filed Sep. 30, 2016, which claims priority to U.S. Provisional Patent Application No. 62/236,782 filed on Oct. 2, 2015, which is hereby incorporated by reference. Priority is claimed pursuant to 35 U.S.C. §§ 119, 371 and any other applicable statute.

STATEMENT REGARDING FEDERALLY SPONSORED RESEARCH AND DEVELOPMENT

This invention was made with government support under Grant Number 1307550, awarded by the National Science Foundation. The government has certain rights in the invention.

FIELD OF THE INVENTION

The technical field generally relates to devices and methods that generate and utilize shaped three-dimensional (3D) microparticles with complex shapes, topologies, and material composition or properties.

BACKGROUND

Shaped microparticles with complex curvature, holes, and surface or composite heterogeneity enable unique applications in biomaterials, self-assembly, photonic crystals, and encoding. Microparticles with shape control and multi-functionality have been engineered to enable advanced technologies, including self-aligned flow cytometry and encoded-microparticle-based multiplexed detection. Drug delivery and cell uptake are known to be shape-dependent while assembly of tissue mimetic systems could benefit from 3D interlocking shapes and spatially engineered combinations of constituents. Moreover, for scaling up production of therapeutic compounds in cell bioreactors, particles shaped with pores or voids could enhance cell growth, achieving high surface area while protecting cells from high fluid shear stress.

Additive layer-by-layer fabrication processes, such as 3D printing, have allowed for the manufacturing of complex three-dimensional and software-designed objects with holes or voids from a variety of materials, but mass-production of microscale objects or features are difficult to achieve. Optical lithography approaches that leverage microfluidic delivery of precursor photopolymer streams, such as stop-flow lithography (SFL), possess many of the advantages of 3D printing technologies, and have expanded fabrication to microscale objects (i.e. particles) with a relatively high manufacturing rate that is on an upward trajectory. In SFL, a flowing stream of oligomer is stopped prior to polymerizing an array of particles into it. See Dhananjay et al., Stop-flow lithography in a microfluidic device, Lab Chip, 7, 818-828 (2007). Although recent work has expanded optofluidic lithography approaches, initially limited to extrusions of 2D patterns, to a larger set of 3D shapes, the particle shapes that are achievable remains limited compared to 3D printers.

Structure-induced flow deformation has been used to shape co-flows of UV-crosslinked polymer precursor streams and inert streams to create three-dimensional fibers and millimeter-scale particle shapes following flood or masked UV exposure subsequent to flow stoppage respectively. The flow deformation can be precisely predicted within a laminar flow regime, Reynolds number, $Re<\sim 2000$, where Re is the ratio of inertial to viscous effects in the channel. More recently, a process for the fabrication of shaped microfibers has been developed that combines software-enable inertial microfluidics and photopolymerization. See Nunes et al., Fabricating Shaped Microfibers with Inertial Microfluidics, Advanced Materials, Vol. 26, 3712-3717 (2014). This approach was also used to predict and design shaped fibers. When transitioning from fibers to shaped particles the velocity gradients within the channel require flow stoppage before polymerization, since the timescale for polymerization is also comparable or longer than the timescale of the flow, and the fluid will slip different amounts before solidifying, leading to elongated or distorted shapes.

However, a significant challenge for inertial-microfluidics-based lithography is to shrink down the size of fabricated particles to the micrometer scale. Specifically, higher viscosity solutions of the polymer precursors that must be shaped at higher Reynolds number than standard stop-flow lithography lead to pressures that significantly flex the fluidic system leading to long capacitive times and the inability to quickly stop the shaped flow before it transits out of the channel. Prior attempts to address this problem while still achieving a high Reynolds number necessary to shape a flow and stop flow in a reasonable time was to enlarge the channel size. However, this led to particles that were fabricated at the millimeter scale and required a longer flow development and settling time due to longer timescales for viscous dissipation of fluid momentum. Methods are needed to achieve the production of shaped particles having a much smaller size.

SUMMARY

In one embodiment, a method of forming three-dimensional shaped microparticles in a microfluidic device includes flowing a mixture of a monomer and photoinitiator in a microfluidic channel of the microfluidic device having a plurality of pillars disposed therein to define a flow stream having a pre-defined shape. The method further includes temporarily stopping the flow stream and polymerizing one or more portions of the flow stream located downstream of the plurality of pillars by passing polymerizing light through one or more masks and onto the flow stream, the polymerization process forming a plurality of three-dimensional shaped microparticles. Flow of flow stream is then restarted. This process may be repeated a number of times.

The three-dimensional shaped microparticles that are generated may optionally include a protected region formed on each of the three-dimensional shaped microparticles. The protected region may include a notch, valley, a flexible region, or the like. In one embodiment, a cell or multiple cells may then be adhered to the protected region using a cellular binding moiety that is located in the protected region. In one embodiment, the three-dimensional shaped microparticles having adhered thereto one or more live cells may be interrogated at a downstream location in a microfluidic device. The cells are protected from shear and other fluidic stresses that may otherwise kill or damage the cells.

Interrogation may include imaging the three-dimensional shaped microparticles or measuring fluorescent light emitted from the one or more cells.

In another embodiment of the invention, the three-dimensional shaped microparticles may incorporate magnetic nanoparticles therein. The three-dimensional shaped microparticles may then be manipulated using an externally applied magnetic field.

In one embodiment, the microfluidic device is coupled to one or more pumps that pump the mixture of a monomer and photoinitiator (and optional binding moieties) through the microfluidic device, the microfluidic device further including an output path from the outlet and a valve is disposed in the output path. The flow is temporarily stopped by automatically closing the valve and stopping the pump. When the flow is stopped, polymerizing light is turned on and passes through one or more geometrically designed masks that interact with the downstream flow stream to form a three-dimensional shaped microparticle (or multiple three-dimensional shaped microparticles). The flow may be restored to flush the newly generated three-dimensional microparticles downstream or out of the microfluidic device. The process may be repeated a number of cycles.

In another embodiment, a system for forming three-dimensional shaped microparticles in a microfluidic device includes a microfluidic device such as a chip having one or more inlets, an outlet, and a microfluidic channel connecting between the one or more inlets and the outlet, the microfluidic device having a plurality of pillars disposed therein to define a downstream flow stream having a pre-defined shape. The system includes a computer-controlled polymerization system interfacing with the microfluidic device, the computer-controlled polymerization system includes one or more computer-controllable pumps coupled to the one or more inlets; a light exposure system configured to selectively expose the downstream flow stream having the pre-defined shape to polymerizing light passing through one or more masks; and a computer-controlled valve configured control flow from the outlet of the microfluidic device.

BRIEF DESCRIPTION OF THE DRAWINGS

FIG. 2E illustrates a perspective view of a microchannel carrying a three dimensional microparticle in the shape of a barbell that includes a recessed or protected region where a cell is adhered to.

FIG. 7A illustrates C/Triangle microparticles made of PEGDA viewed from multiple angles. FIGS. 7B and 7C illustrates diamond/ellipsoid microparticles composed of thiolene polymer.

DETAILED DESCRIPTION OF THE ILLUSTRATED EMBODIMENTS

Figure 1:
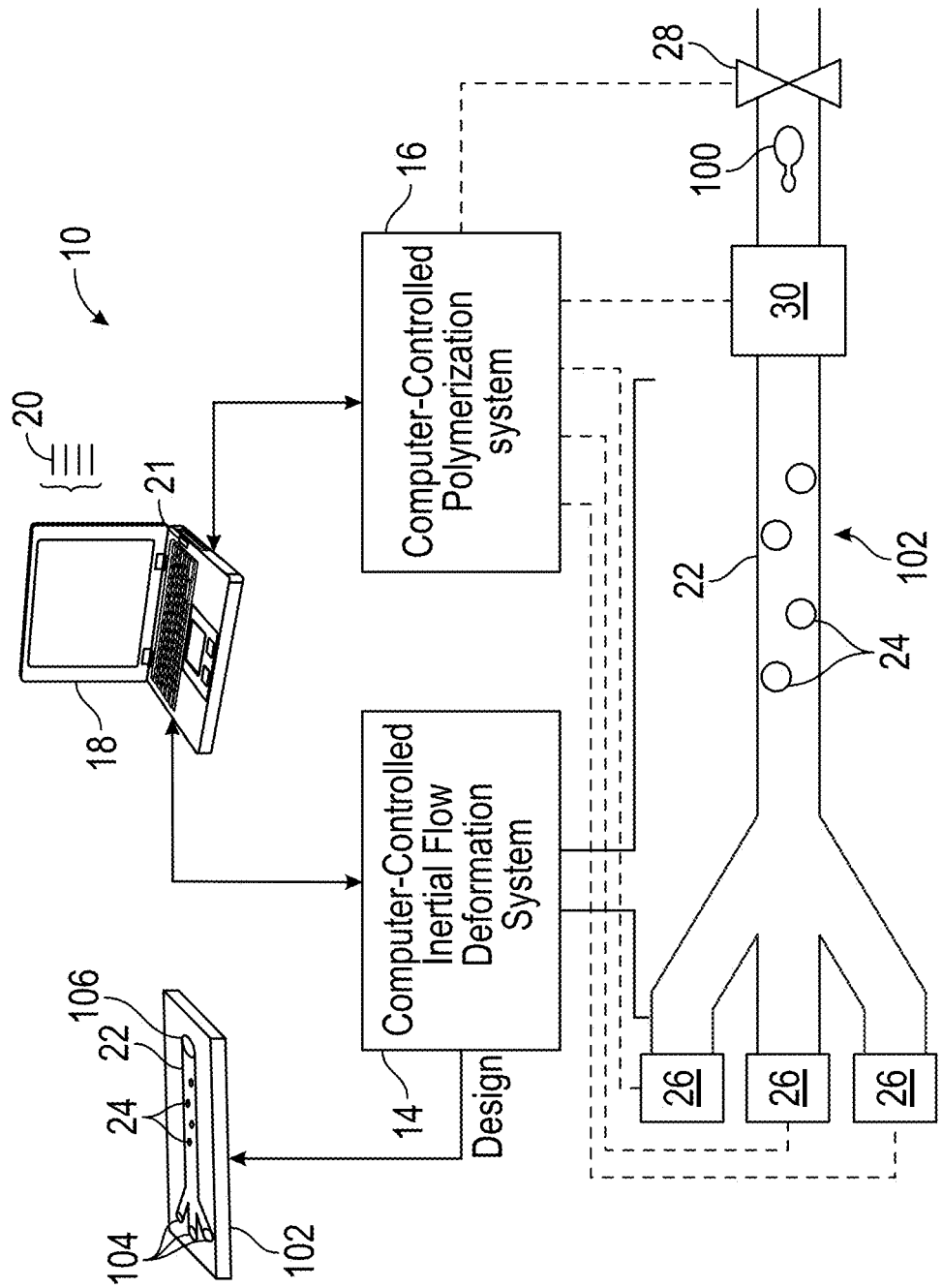
FIG. 1 illustrates a schematic illustration of a fabrication system for forming three-dimensional shaped microparticles in a microfluidic device according to one embodiment.

FIG. 1 schematically illustrates a fabrication system 10 for forming three-dimensional shaped microparticles 100 in a microfluidic device 102 that is according to one embodiment using optical transient liquid molding of microparticles 100. The microparticles 100 may have complex three-dimensional shapes with 100-micrometer or smaller scale dimensions. The microparticles 100 may be less than about 200 μm in their longest dimension. The fabrication system 10 includes two sub-systems: a computer-controlled inertial flow deformation system 14 and a computer-controlled polymerization system 16. The inertial flow deformation system 14 includes at least one computer or computing device 18 that contains software 20 or executable code using one or more processors 21 within the computer or computing device 18 that is used to generate a design for a microfluidic channel 22 of the microfluidic device 102 that contains therein a plurality of obstructions such as pillars 24 that are used to yield a desired cross-sectional or sculpted flow shape after flowing through the microfluidic channel 22. In one aspect of the invention, the user is able to input to the software 20 a desired geometric shape or profile of the cross-sectional flow that is desired and the software 18 outputs a design for the microfluidic channel 22 that includes details on the size of the microfluidic channel 22 as well as the size, sequence, and positioning of pillars 24 (or other obstructions) within the microfluidic channel 22 that can be used to generate the desired cross-sectional flow. As an alternative to inputting the desired cross-sectional flow, the user may also input the desired shape of microparticle 100 and the software 20 outputs a design for the microfluidic channel 22. The user may also use the software 20 to manually place, adjust, and tune the location, size, and positioning of obstructions such as pillars 24 as well as other parameters to create the microfluidic channel 22 that produces the desired effects.

The system 10 further includes a computer-controlled polymerization system 16. The computer-controlled polymerization system 16 interfaces with the microfluidic device 12 and is used to control the flow of reagents and other solutions through the microfluidic channel 22 of the microfluidic device 12. For example, pumps 26 are used to deliver reagents and other solutions into the microfluidic device 12 to generate the sculpted flow shape. The computer-controlled polymerization system 16 is used to turn pumps 26 on/off as well as adjust flow rates through the microfluidic device 12. One or more valves 28 are integrated into the flow path that contains the microfluidic channel 22. These valves 28 may be positioned on-chip (i.e., on the microfluidic chip 102) or off-chip. In one preferred aspect of the invention, one or more valves 28 are situated in a downstream region of the flow path that is located after the region where the microparticles 100 are formed. For example, a valve 28 may be positioned downstream from an outlet from the microfluidic device 12 and may squeeze or pinch a flexible tubing or conduit that is secured to the outlet 106 of the microfluidic device 102. The computer-controlled polymerization system 16 is used to control the valves 28 (e.g., turn valves on/off).

The computer-controlled polymerization system 16 is also used to control various aspects of a light exposure system 30. The light exposure system 30 is used to selectively expose the sculpted fluid flow that is created within the microfluidic channel 22 to polymerizing light. As explained herein in more detail, the polymerizing light passes through a mask (or multiple masks) which creates a specific geometric-shaped area of polymerizing light that interacts with the sculpted flow to polymerize and create the microparticle 100 having the desired three-dimensional shape for the microparticle 100. The computer-controlled polymerization system 16 is used to control, for example, the intensity and exposure time of the polymerizing light that is used to form the three-dimensional shaped microparticles 100.

In one embodiment, the same computer or computing device 18 that is used for the computer-controlled inertial flow deformation system 14 is also used for the computer-controlled polymerization system 16. Alternatively, there may be a separate computer or computing device 18 that is used to control the computer-controlled polymerization system 16. For example, the computer or computing device 18 such as a server may run the software that is used to generate the design of the microfluidic device 102. This design is then used to manufacture the microfluidic device 102 using known methods of manufacturing microfluidic devices.

For example, the microfluidic device 102 may be formed using well known polydimethylsiloxane (PDMS) based soft lithography techniques. For example, molds can be made using two layers of photoresist (SU-8 2100, MicroChem Corp.) that are patterned by photolithography on a wafer. Precursor and curing agent of Polydimethylsiloxane (PDMS, Sylgard 184, Dow Corning) mixed at a 10:1 v/v ratio, is then poured onto the mold, left in a vacuum, and then cured in a 65° C. oven. The replicated PDMS chip or microfluidic device 102, punched at inlets and outlet with 1/32" holes, and a slide glass were treated with air plasma (Plasma Cleaner, Harrick Plasma) for 30 seconds and then bound together to enclose the all microfluidic channels. The inlets 104 of the microfluidic device 102 can be connected to syringe pumps 26 using PEEK tubing (0.08"×0.124", Cat. Number: 1544, IDEX Health & Science). Likewise, tubing (e.g., Tygon tubing (Cat. Number: SC0016, IDEX Health & Science)) is inserted into the outlet 106 of the microfluidic device 102 and leads to the pinching valve 28 (any type of valve can be used). After the pinching valve 28, the tubing leads to a separate particle-collecting filter (not shown) where the microparticles 100 are collected. While a PDMS-based soft lithography technique to manufacture the microfluidic device 102 has been described above, the microfluidic device 102 may be manufactured using any known method of making such devices including 3D printing, molding, etc. Note that the microfluidic channel 22 that contains the obstructions or pillars 24 is longitudinally straight and has a rectangular cross-section. For example, the microfluidic channel 22 may have a width of around 1200 μm and a height of around 300 μm. The pillars 24 located in the microfluidic channel 22 may have varying diameters and may extend either fully or partially along the height direction of the microfluidic channel 22.

Figure 2A:
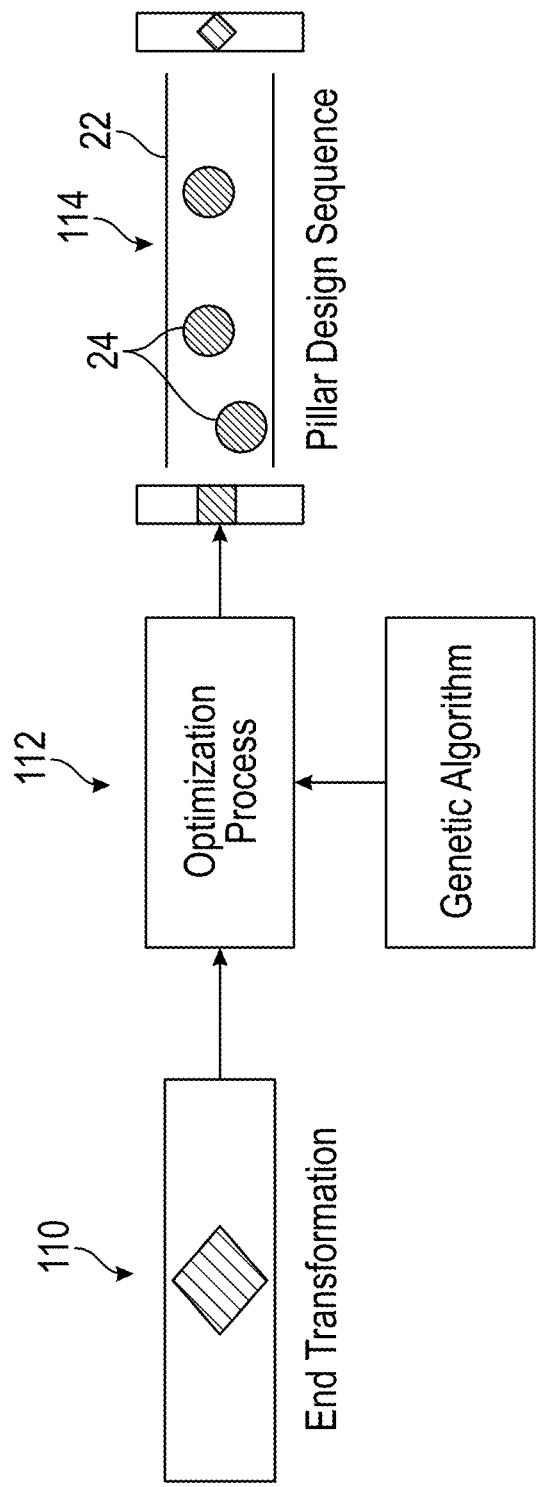
FIG. 2A illustrates a schematic representation of how the computer-controlled inertial flow deformation system generates a microfluidic device design that incorporates a sequence of pillars to generate a desired flow transformation or a final flow profile from an input flow profile.

With reference to FIG. 2A, the computer-controlled inertial flow deformation system 14 is used to aid in the design of the microfluidic device 10. The software 20 or executable code of the computer-controlled inertial flow deformation system 14 operates by generating a configuration of pillars 24 in a microfluidic channel 22 that is based on a desired or end flow transformation 110 as illustrated in FIG. 2A. The desired end flow transformation 110 may be used to create different shapes of microparticles 100. Not only can the shape of the microparticles 100 be designed, the microparticles 100 can be created with different layers or components. Input reagents can be polymerized so that they appear on certain exposed areas of the microparticles 100. For example, molecular binding molecules or moieties can be designed to present on certain geographical regions or faces of the microparticles 100.

The software 20 operates by developing a forward model for the rapid evaluation of arbitrary pillar 24 sequences and formulation of the design as an optimization problem as illustrated in operation 112 of FIG. 2A. Advection maps previously created of individual pillars 24 are converted to sparse transition matrices which store fluid state displacement information as transition probabilities across states. These matrices can then be multiplied together to quickly propagate net deformation across multiple pillars 24. This avoids the computational complexity of dealing with complicated three-dimensional flow simulations. The matrices can then be used with a genetic algorithm or other optimization algorithm as part of the optimization process to generate the optimal configuration of multiple pillars 24 as illustrated in operation 114. The final design which is generated by the computer-controlled inertial flow deformation system 14 can then be used to generate the real-world microfluidic device 102. For example, the software 20 may output a .DXF file that can be used to manufacture the microfluidic device 102. An example of this type of software 20 that may be used to design the microfluidic device 102 includes the uFlow freeware software program available at http://biomicrofluidics.com/software.php. Additional details regarding the programming of flow may be found in U.S. Patent Application Publication No. 2014/0230909 which is incorporated herein by reference. The uFlow program is a graphical tool for the rational design of inertial microfluidic devices that utilize pillar geometries to deform the laminar flow field. The uFlow software program 20 assembles pre-computed advection maps to enable fast, real-time feedback of flow deformation without requiring an online Navier-Stokes equation solver.

Figure 2B:
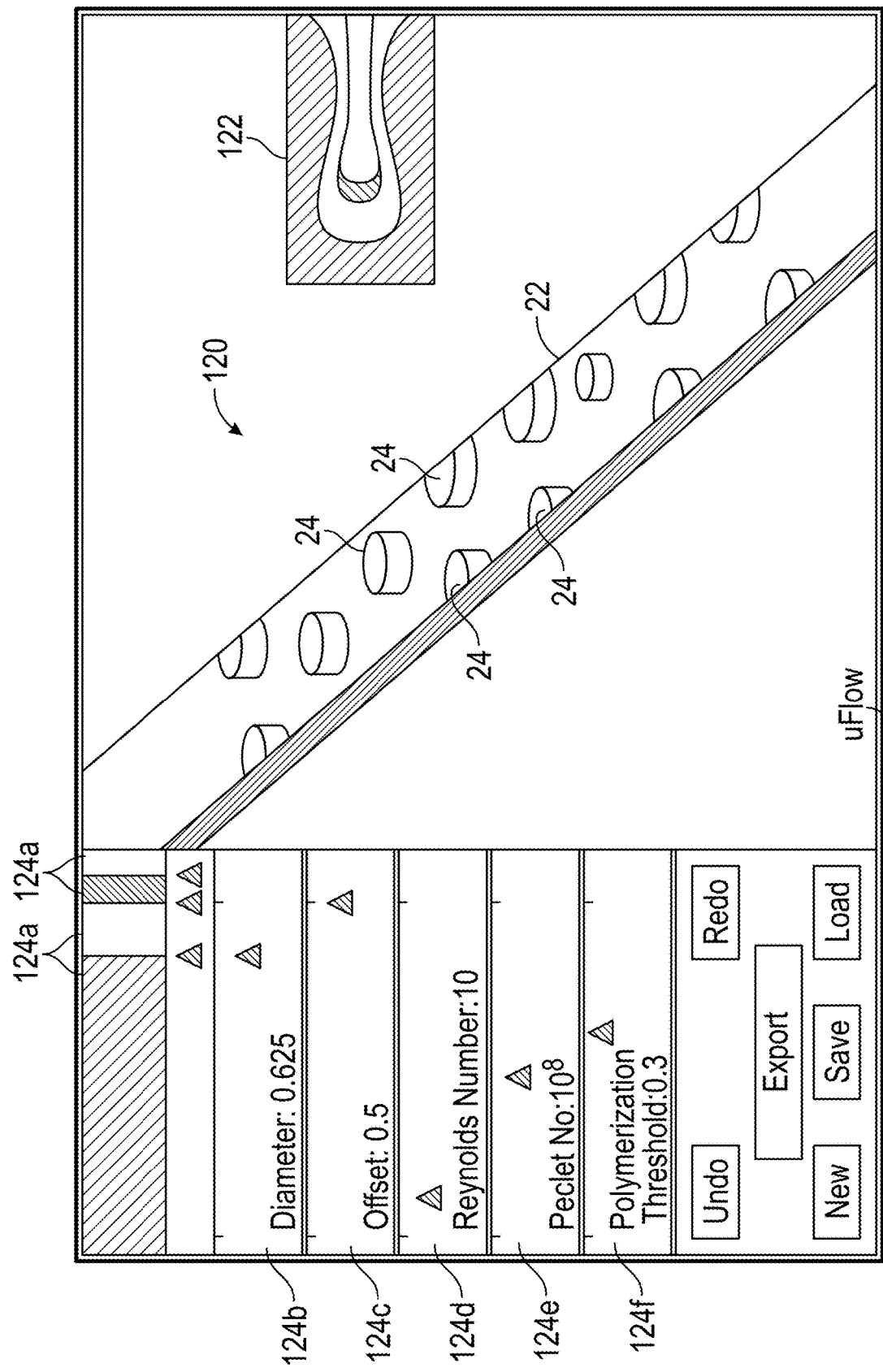
FIG. 2B illustrates a view of the graphical user interface (GUI) of a software program used to generate the microfluidic device that produces the desired flow transformation or a final flow profile.

FIG. 2B illustrates an embodiment of a graphical user interface 120 of the uFlow software program 20 which illustrates also how a user can generate pillar 24 configurations to design end flow profiles in real-time. FIG. 2B, for example, illustrates an example pillar 24 configuration that is used to generate an end flow profile as illustrated in a top down view 122 within the microfluidic channel 22. The user is also given the ability to modify or alter various parameters of the software model. This includes, for example, the number of input streams 124*a* (four are used in this example), the diameter 124*b* of the pillars 24, the offset 124*c* of the pillars 24 from the edge of the microfluidic channel 22, the Reynolds number 124*d*, the Peclet number 124*e* (e.g., for changes in flow or different photoinitiators), and polymerization threshold 124*f* (minimum level needed to achieve polymerization). The relative amount of convection of the photoinitiator in the flow downstream versus diffusion cross-stream is described by the Peclet number, $Pe=U_0W/D$, where D is the diffusion coefficient of the photoinitiator ($D=\sim 10^6$ cm$^2$ s$^{-1}$) and W is the width of the microchannel. The graphical user interface 120 further includes options to load a pillar design ("Load" button), save a design ("Save" button) and export a design in .DXF format ("Export button"). In this particular illustrated embodiment, the shape of the final flow profile 122 is displayed in the GUI 122 in a window. This particular final flow profile 122 is used to make a dumbbell shaped microparticle 100 which is described in more detail herein.

Figure 2C:
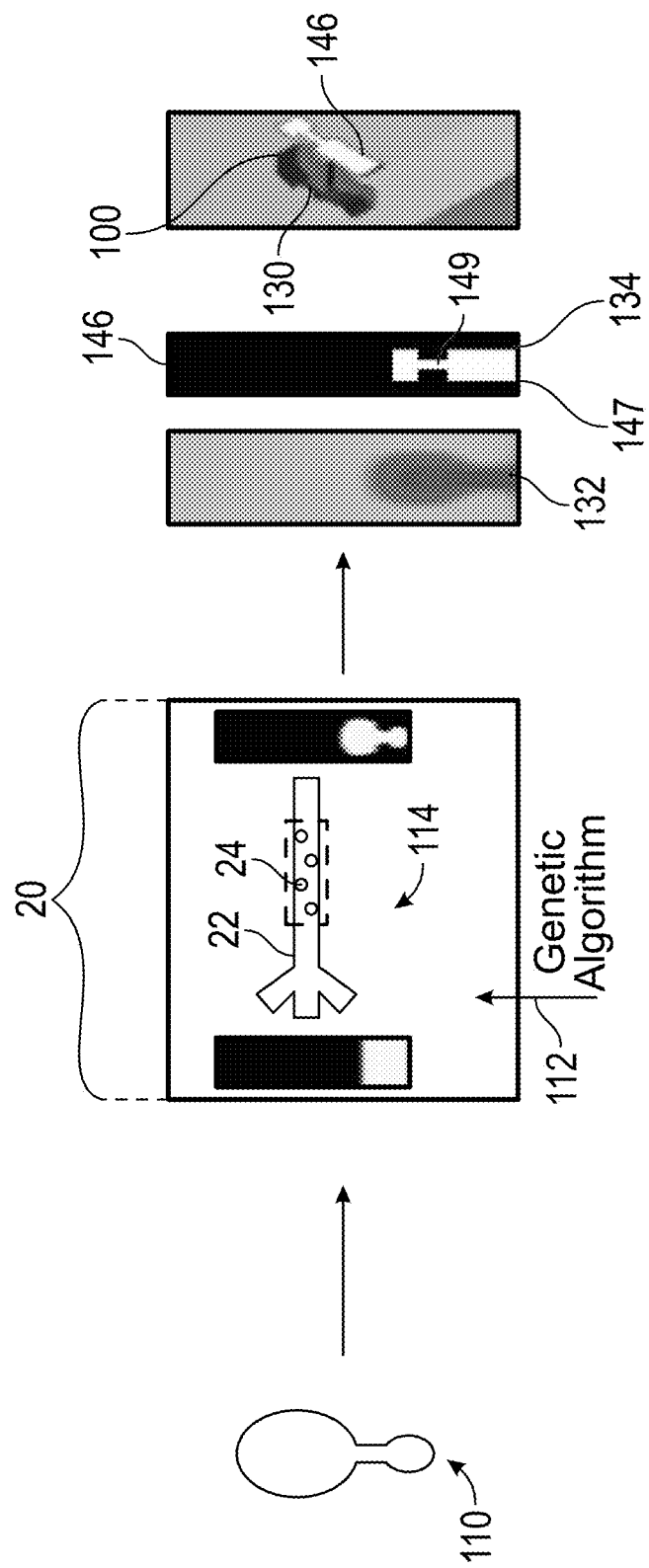
FIG. 2C schematically illustrates how the computer-controlled inertial flow deformation system generates a microfluidic device design that incorporates a sequence of pillars to generate a desired "barbell" flow transformation or a final flow profile from an input flow profile.

FIG. 2C schematically illustrates how an asymmetric microparticle 100 is formed that includes a protected region 130 that is used, for example, as a loading zone for cells 136. The protected region 130 is formed in a notch, groove, pore, valley, hole, flexible region, or other feature that isolates the protected region 130 from larger shear stresses that would otherwise be imparted on the more exposed surfaces of the microparticle 100. The protected region 130, in one embodiment, permits cells 136 to bind to these areas as explained herein whereby the cells 136 are protected from the high shear forces that would otherwise kill the cells 136. While cells 136 are described as binding to the protected region 130, the protected region 130 may also be used to bind molecules, particles, beads, and the like. As seen in FIG. 2C, the desired or end flow transformation 110 is established in operation 110. This end flow pattern will produce the asymmetric microparticle 100 when polymerized. The software 20 uses a forward model for the rapid evaluation of arbitrary pillar 24 sequences and optimizes this using a genetic algorithm as illustrated in operation 112. The illustrated end flow profiles that are created by the optimized pillar sequences 24 is illustrated in the top down view 132, cross-sectional side view 134, and the perspective view of the asymmetric microparticle 100. Also illustrated is the mask 146 that is used to polymerize the shaped flow into a microparticle 100.

Figure 2D:
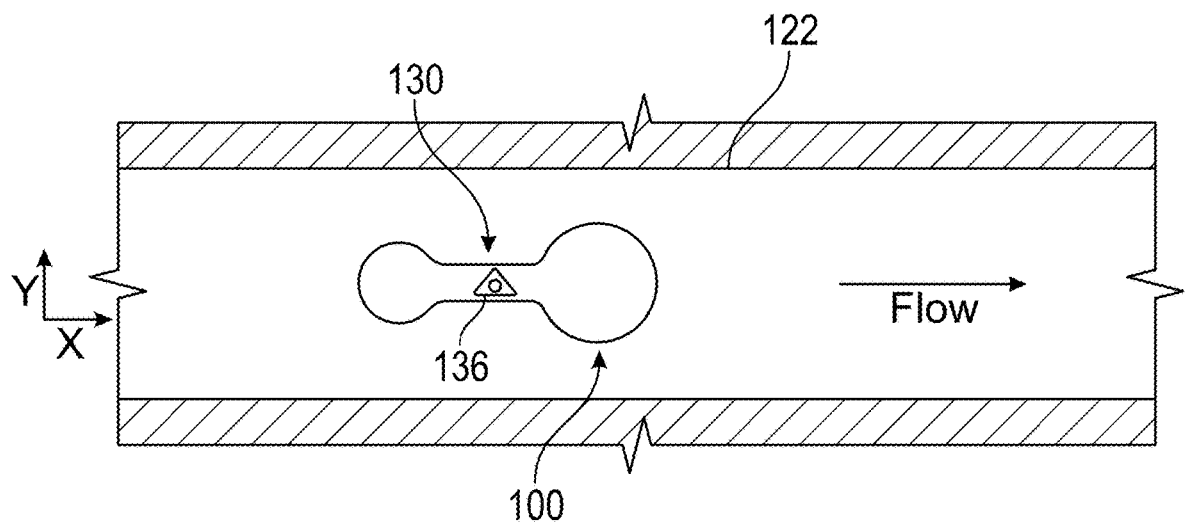
FIG. 2D illustrates a top view of a microchannel carrying a three dimenssional microparticle in the shape of a barbell that includes a recessed or protected region where a cell is adhered to (multiple cells or groups of cells may also adhere to this region). The microparticle is asymmetric in the x direction.
Figure 2E:
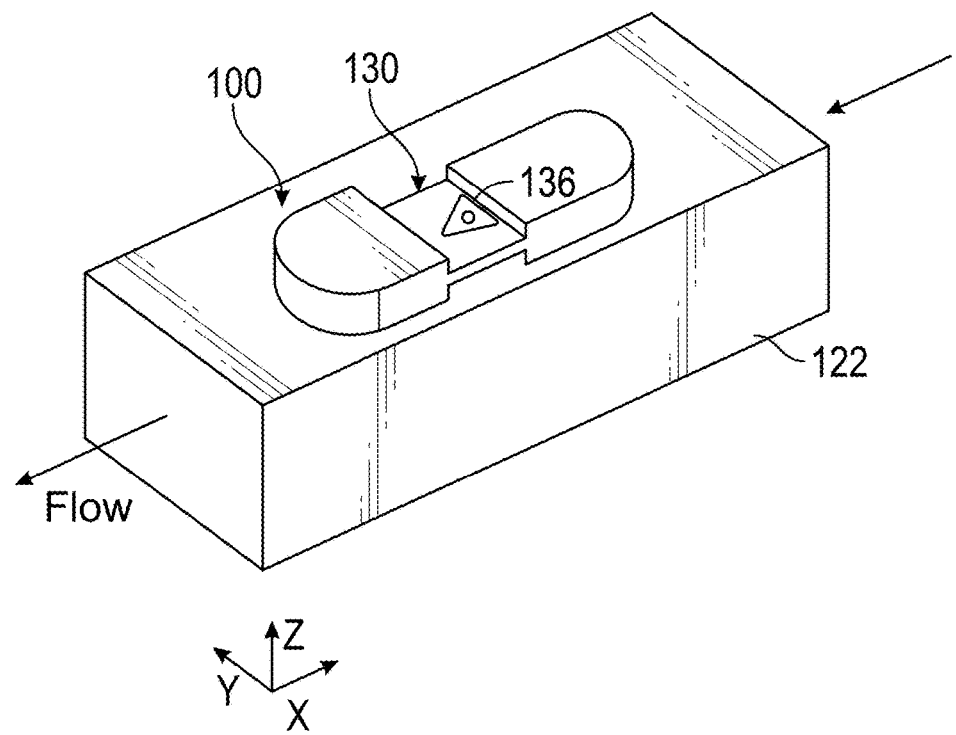

FIGS. 2D and 2E illustrate an example of an asymmetric microparticle 100. FIG. 2D illustrates a top view of a microfluidic channel 22 carrying a three dimensional microparticle 100 in the shape of a barbell that includes a recessed or protected region 130 where a cell 136 (or other species) is adhered to (multiple cells or groups of cells 136 may also adhere to this region 130). The microparticle 100 is asymmetric in the x direction. FIG. 2E illustrates a perspective view of a microfluidic channel 22 carrying the asymmetric, three dimensional microparticle 100.

Figure 3A:
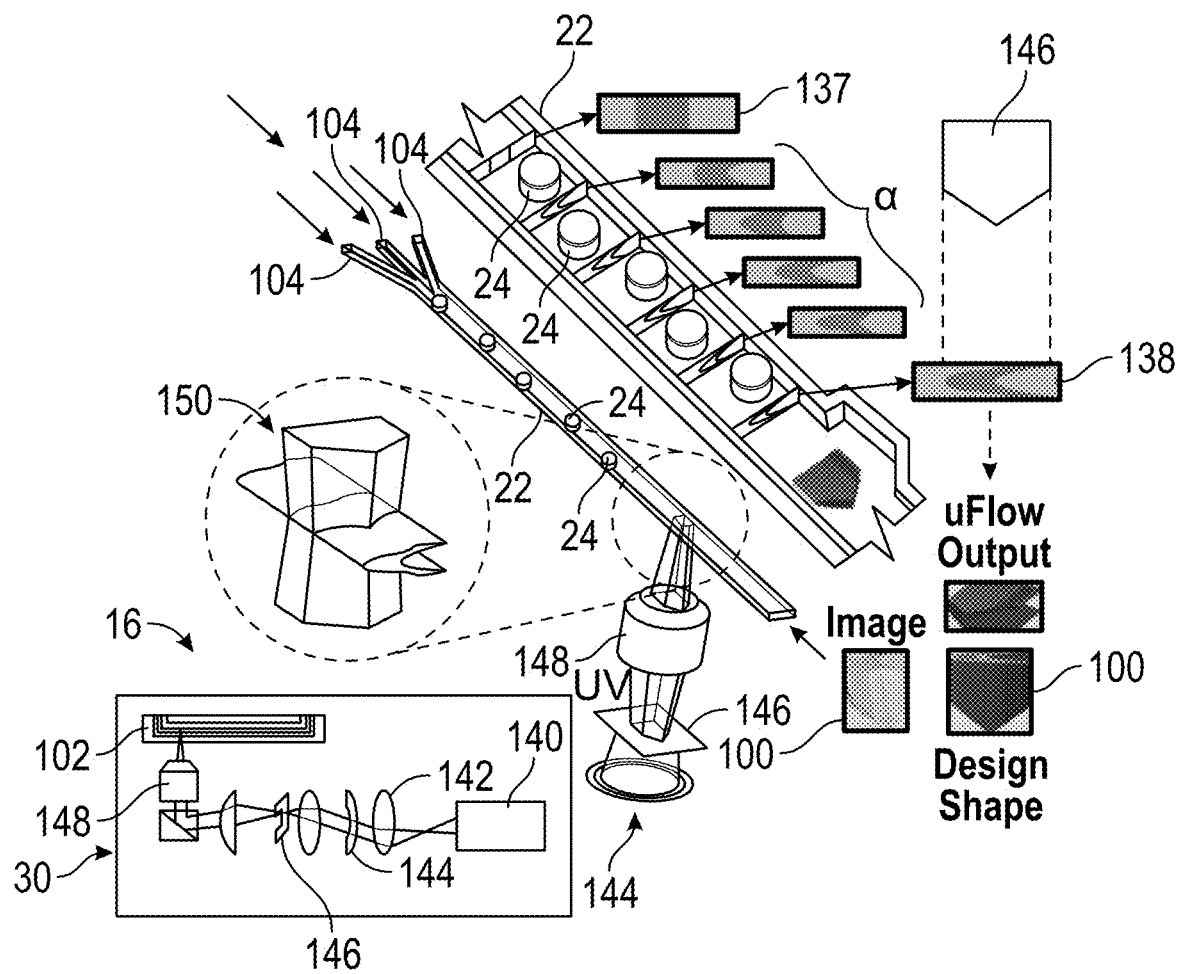
FIG. 3A illustrates a schematic illustration of a fabrication system for forming three-dimensional shaped microparticles in a microfluidic device according to one embodiment another embodiment. This embodiment uses a UV-based light exposure system 30.

FIG. 3A illustrates various aspects of the computer-controlled polymerization system 16 that is used to create a three dimensional microparticle 100. The microfluidic channel 22 is illustrated that has been fabricated after having the configuration of pillars 24 designed by the computer-controlled inertial flow deformation system 14 described previously. Cross-sectional views a of the flow streams passing through the microfluidic channel 22 at various downstream points are illustrated. In this embodiment, three separate inlets 104 are combined in the flow of the microfluidic channel 22. This includes two outer inlets 104 that carry only the monomer that is to be polymerized. The center inlet 104 carries the monomer and a photoinitiator that is required for polymerization of the monomer in response to light exposure.

The monomer may be part of an aqueous-based system where monomer poly(ethylene glycol) diacrylate (PEGDA, MW-575, 437441, Sigma-Aldrich) is diluted in an aqueous solution, for example diluted (with PBS) which is used in the target precursor stream (center) with a photoinitiator made from 0.67% 2-hydroxy-2-methylpropiophenone (Darocur 1173, 405655, Sigma-Aldrich). The side streams include diluted PEGDA. The monomer may also be part of an organic-based system such as PEGDA ($M_n$=250) diluted with ethanol in combination with 5 wt % of 2,2-Dimethoxy-2-phenylacetophenone (DMPA, 196118, Sigma-Aldrich). Diluted PEGDA may also be used in the side streams. Another example of an organic system includes UV optical adhesive (NOA89, Norland) which is used in the center target precursor stream along with 5% wt of 2,2-Dimethoxy-2-phenylacetophenone (DMPA, 196118, Sigma-Aldrich). The two side streams may include triethylene glycol dimethacrylate (TEGDM, 261548, Sigma-Aldrich).

Another example of a material that may be used to form the microparticles 100 includes flowing a photoresist in the center or target precursor stream with polyethylene glycol (PEG) being used in the side streams. Various oligomers such as epoxides, urethanes, polyethers, or polyesters which are typically functionalized by an acrylate may also be used in the central target precursor stream. The photoinitiator may include benzophenone, xanthones, quinones, benzoin ethers, acetophenones, benzoyl oximes, and acylphosphines. Oligomers without a photoinitiator may be used in the side streams. Additionally, monomers including styrene, N-vinylpyrrolidone, and acrylates may be used with the photoinitiators described above. Monomers without the photoinitiator may be used in the side streams.

As seen in FIG. 3A, the input flow design 137 changes into the final shape 138. A light exposure system 30 is provided to illuminate the flow at a location where the final flow shape 138 takes form. The light exposure system 30 includes a light source 140 such as an ultraviolet light (UV) source that passes through a lens 142 and a controllable shutter 144 which is used to adjust exposure times. The light passing through the shutter 144 then passes through a mask 146 that contains a specifically shaped aperture formed therein that defines the shape of the light that will be exposed to the flow of fluid within the microfluidic channel 22. The now-masked light may pass through optical components such as an objective lens 148 (other lenses or mirrors commonly known to those skilled in the art may also be disposed in the optical path) to focus the masked light onto the sculpted flow in the microfluidic channel 22. This creates an orthogonal intersection 150 between two extruded two-dimensional (2D) shapes, namely the masked light source and the sculpted flow. These two 2D shapes may be non-rectangular to produce a three dimensional microparticle 100 that is formed by the light initiated polymerization reaction. The three-dimensional shape of the microparticle 100 may be geometrically complex by using non-rectangular 2D orthogonal shapes for the flow and/or masked light source. While FIG. 3A illustrates a single mask 146 being used, there could be multiple masks 146 that are used to generate a plurality of three dimensional particles 100 at the same time. In this embodiment, a common mask substrate having a series of holes or apertures formed therein to create the individual masks 146 that are in a linear arrangement or configuration and may be overlaid over the microfluidic channel 22 in the longitudinal or flow direction. A collimated beam of polymerizing light then passes through the masks 146 to create three dimensional particles 100 at each intersecting location with the developed fluid flow.

In the multiple masks 146 embodiment, the masks 146 are aligned in a linear pattern that corresponds to the direction of the shaped fluid stream. The high Peclet number of the flow (Pe>>1), allows for the shaped stream to maintain its structure for a long downstream distance (e.g., centimeters), and enables the linear array of multiple masks 146 to create uniformly shaped particles along the length of the shaped stream following light exposure.

Figure 3B:
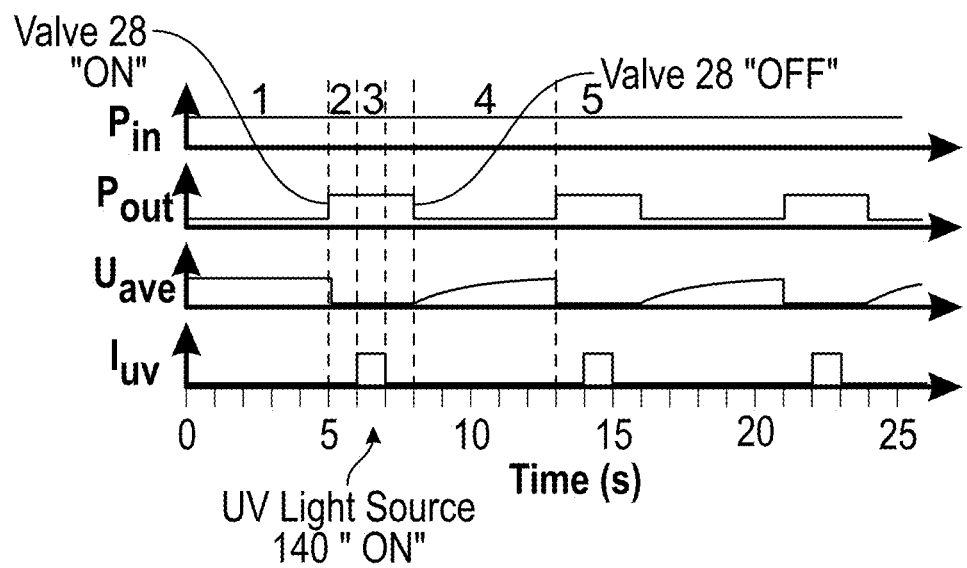
FIG. 3B illustrates plots of four system parameters as a function of time. These include: inlet pressure $P_{in}$, outlet pressure $P_{out}$, average flow velocity $U_{ave}$, and UV intensity $I_{UV}$, for the cycled four (4)4 steps required for three-dimensional shaped particle fabrication. Step five (4) represents another cycle of the four (4) steps in the plot.

Note that the light is turned on or flashed only when the flow in the microfluidic channel 22 is stopped or substantially reduced to zero. Microparticles 100 are not formed while the fluid is flowing in the microfluidic channel 22. This is because the polymerization process is not instantaneous and well-defined microparticles 100 cannot be formed (the microparticle shapes will be blurred). With reference to FIG. 3B, four steps are run in series to finish a single process. Illustrated are $P_{in}$ which represents pressure at the inlet 104. $P_{out}$ represents pressure at the outlet 106. $U_{ave}$ represents the average flow rate through the microfluidic channel 22. $I_{UV}$ represents the state of the UV light source (either ON or OFF). FIG. 3B illustrates these parameters as a function of time.

First, the monomer precursor and the photoinitiator are pumped through the microfluidic channel 22 using the pumps 26. The pumps 26 may include computer-controlled syringe pumps such Harvard Apparatus, PHD 2000 at a set Reynolds number (Re) to form the precursor stream with a pre-designed cross-section once the flow has been fully developed. It may take several minutes (e.g., 5 minutes) to completely pressurize the microfluidic channel 22 and reach a fully-developed flow. In a second step, the syringe pump(s) 26 are turned off and the downstream valve 28 (FIG. 1) is switched closed; pressurizing downstream of the microfluidic channel 22 to stop the flow without disturbing the shape of the flow stream. The flow stream remains under high pressure as compared to atmospheric pressure while the flow stream is temporarily stopped.

After turning off flow, there is a short waiting period for about one (1) second for flow to stop. The more quickly the flow is stopped and UV exposure is applied, the more faithfully the created microparticle 100 will replicate the predicted particle shape. On the other hand, the time period to stop the flow and UV illumination delay time can also be used to tune the shape of the microparticle 100. A diffusion time of ~1 s was used (diffusive distance after the flow stops of 110 µm) to minimize the error caused by diffusion. For the third step, the shutter 144 is opened allowing UV illumination through an optical mask 146 (or multiple masks 146 if many microparticles 100 are formed at once) which is then demagnified by a 10× objective lens 148 onto the target location of the stream for about 0.5 to about 1.5 seconds. The UV power is set to be 300~800 mW/cm$^2$, measured by a power meter (PM206, ThorLABS). The intersection of the precursor stream and optically-masked shape forms the three dimensional photopolymerized microparticle 100 inside the microfluidic channel. Finally, in step four, the valve 28 is re-opened and the pump(s) 26 restarted to wash the polymerized microparticle 100 downstream and a new liquid mold is reformed 5 to 10 seconds after the downstream valve 28 is switched open and the syringe pump(s) 26 turned on again. These four steps are then automatically repeated to fabricate particles at a rate of approximately 720 particles per hour.

To create larger numbers of microparticles 100 without user intervention, the computer-controlled polymerization system 16 may control the valve 28 (ASCO Scientific®, 2-Way Pinch Valve, Catalog Number: SCH284A003) that is connected to the outlet of the microfluidic device 102 with a 10 cm Tygon tubing to stop flow, and control of a shutter 144 (Lambda SC, Smart Shutter™ control system) for UV illumination (Excelitas Technologies, OmniCure® S2000 UV Curing System) of the stationary liquid mold. The outlet of the valve 28 is connected to a microparticle collector reservoir (now shown) which includes a filter to accumulate microparticles 100. The time plots of the system parameters over the four steps are shown in FIG. 3B. The longest step is in re-establishing the steady-state flow shape defining the liquid mold (i.e., step 4), after stopping flow.

Because of the pressure built up during flow stoppage and the maximum pressure rating of the particular pinch valve 28 used in the experiments discussed herein, the working range for precursor solution viscosity when Re equals to 10 was <15 mPa·s. On the other hand, when the capacitive timescale is not dominant, the flow stoppage time is dominated by the timescale of viscous dissipation, $H_h^2/\nu$, where $\nu$ is the kinematic viscosity. Unlike for previous stop flow lithography systems, for these inertial flows, less viscous fluids, such as water (~1 mPa·s), required a longer flow stoppage time and were less ideal.

Figure 4A:
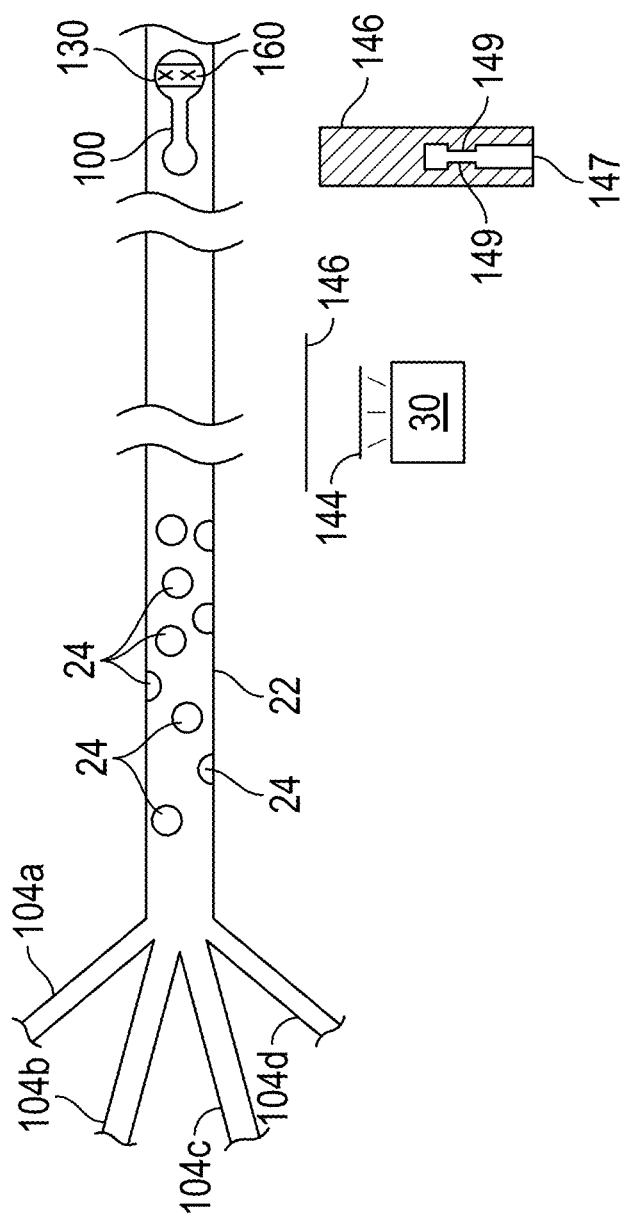
FIG. 4A illustrates a schematic view of a microfludic layout used to generate asymetric microparticles having a protected region for adherent cells according to one embodiment.
Figure 5A:
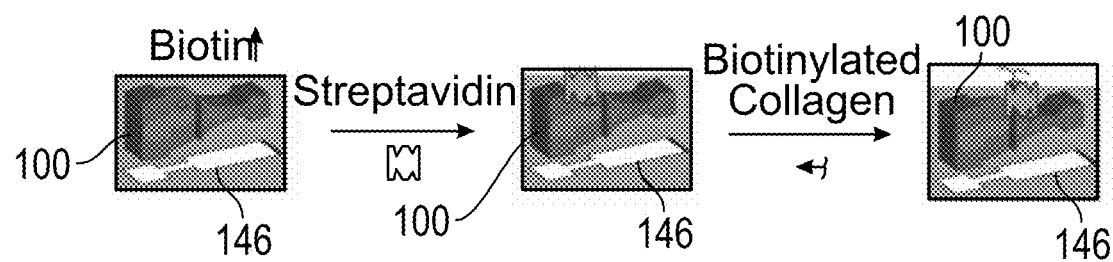
FIG. 5A schematically illustrates how a three dimensional microparticle having biotin-labelled surface area or region is linked to streptavidin followed by a cellular binding moeity (e.g., biotinylated collagen).
Figure 5B:
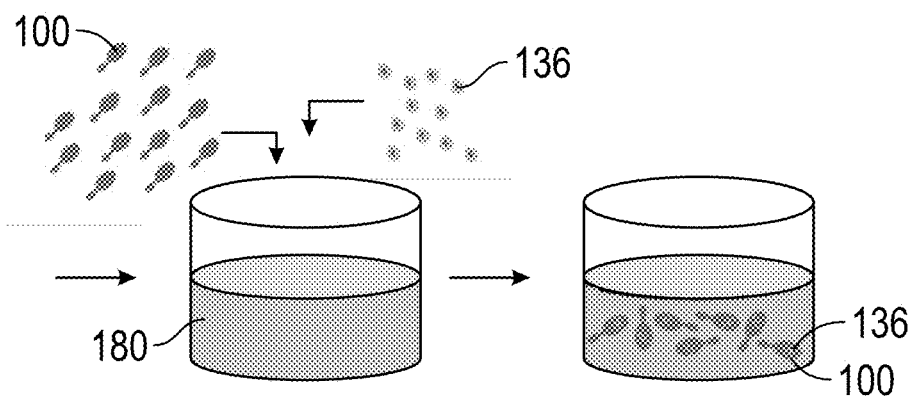
FIG. 5B illustrates how three dimensional microparticles are incubated with cells to form three dimensional microparticles with adherent cells within a protected region of the microparticles.
Figure 5C:
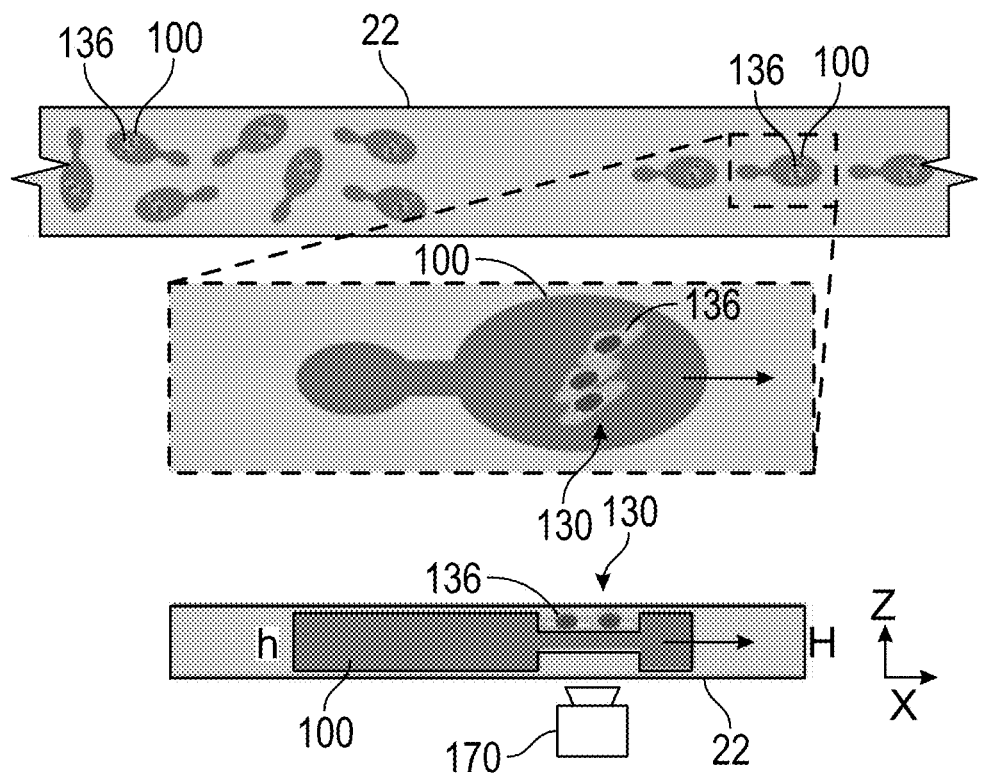
FIG. 5C illustrates top and side views of an asymmetric, three dimensional microparticle passing through a microfludic channel for downstream analysis (i.e., optical detection). The microparticle is illustrated as containing adherent cells located in a protected region of the microparticle.

In one embodiment, microparticles 100 or "carriers" are designed to have a three-dimensional shape with a cellular binding moiety or moieties bound on a portion of the surface of the microparticle 100. In one aspect, the cellular binding moiety may include a biotinylated region 160 or multiple such regions enabling attachment of streptavidin and other biotinylated molecules, such as biotinylated collagen such that cells 136 can bind onto a localized region of the microparticles 100. The microparticle 100 is shaped as described previously, namely, through the orthogonal intersection of the fully developed flow with a two-dimensional masked polymerizing light. FIG. 4A illustrates one embodiment of a fabrication system 10 that is used to create microparticles 100 that contain a protected region 130 that is used as a loading zone for cells 136. The protected region 130 contains a biotinylated region 160 that is formed during the polymerization process. In this embodiment, the microparticle 100 is asymmetrically shaped as a dumbbell. The asymmetric dumbbell shape achieves self-steering (i.e., orientation along a predicable axis and migration to a particular streamline within flow) in Stokes flow. The biotinylated region 160 of cell binding is designed to be encapsulated in the boundary of the dumbbell and surrounded by regions of the microparticle 100 without binding affinity. According to this design, the mask 146 is a slit 147 with notches 149 on both sides. The width of slit 147 is designed to be ~90% of the height of microfluidic channel 22 such that the created microparticle 100 can reach confining boundaries in a flow-through channel. For example, as seen in FIG. 5C, the height (h) of the microparticle 100 is close to 90% of the height (H) of the microfluidic channel 22.

In this embodiment, there are four separate inlets 104a, 104b, 104c, 104d that lead to the microfluidic channel 22. The upper inlet 104a is coupled a source of monomer (e.g., polyethylene (glycol) diacrylate (PEGDA)) although other photo-linkable polymers may be used. The next inlet 104b is coupled to a source of monomer and a photoinitiator (e.g., 2-hydroxy-2-methylpropiophenone, Darocur 1173 0.67%). Other photoinitiators may also be used. The next inlet 104c is coupled to a source of monomer, photoinitiator, and Biotin-PEG-Acrylate. The Biotin-PEG-Acrylate component was formed using Biotin-Hydrazide (1.25 mg mL$^{-1}$, B7639, Sigma-Aldrich) and Acrylate-PEG-NHS (5 mg mL$^{-1}$, MW-5000, Laysan Bio, Inc.) in Dulbecco's phosphate-buffered saline (DPBS).

The last inlet 104d is coupled to a source of monomer and photoinitiator. Biotin-PEG-Acrylate was synthesized as the additive in the portion of the target flow designed for cell binding (i.e., the biotinylated region 160 of the microparticle 100). The method to increase the fabrication rate is synthesizing hundreds of microparticles 100 instead of a single microparticle 100 using an elongated straight microfluidic channel 22 downstream and polymerizing along the length of the formed stream each time the flow is stopped.

In this embodiment, a large microfluidic chip 102 is fabricated using 6 inch wafer-based soft lithography. The light exposure system 30 uses a collimated UV light source 140 with large exposure area and an optical mask 146 having a row of masks apertures like those of FIGS. 4A and 4B to create the dumbbell shaped microparticles 100. Because of the high Peclet number of the sculpted flows, COMSOL simulation showed that the interface of the co-flows in the cross section can be kept without significant blur caused by diffusion over approximately 6 cm along the straight microfluidic channel 22 downstream. The area for illumination of patterned UV light was enlarged using a microfluidic channel 22 with a 6 cm long downstream section replicated from a photoresist mold made on a 6-inch wafer using photolithography. The microfluidic chip 102 was placed upside down on a x-y translational and rotational optical stage. The polymerizable target and side polymeric liquid (PEGDA with and without photoinitiator) were injected from the bottom. Solution was also exhausted out an outlet in the bottom of the chip passing a pinch valve 28 toward a collection tube.

Figure 4B:
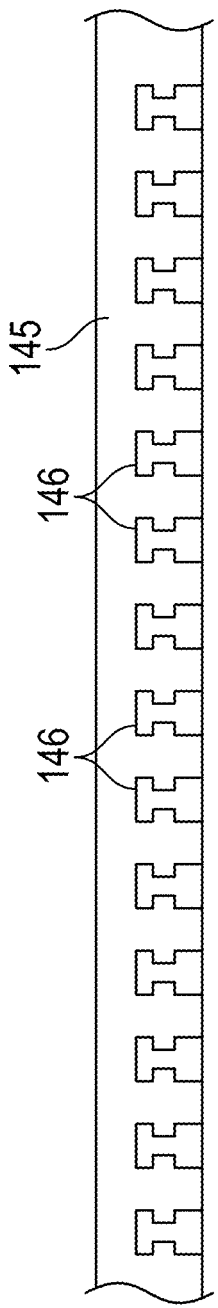
FIG. 4B illustrates a substrate having a plurality of masks formed therein and arranged in a row. This substrate is placed over the microfluidic channel to form a plurality of microparticles with a single exposure to polymerizing light (e.g., UV light).

In addition, to increase the optical exposure area, collimated UV light was generated in a circle with 3 cm in diameter on the top of the microfluidic chip 102 by a high power UV light source with collimation adaptor. The collimated UV light was then passed through a Chrome substrate defining an optical mask 146 as illustrated in FIG. 4B with the plurality of mask apertures formed therein in a row which was placed on the top of the glass substrate of the microfluidic chip 102. Alignment marks (not shown) on the mask 146 and microfluidic chip 102 may be used so the light beams can be located at the same lateral position in alignment with the sculpted precursor stream from the first to the last pattern in the row.

The microparticles 100 are created by the fabrication system 10 in an automated process as described herein. This includes pumping the precursor using a syringe pump 26, stopping flows by holding pumps 26 and pinching the downstream tubing using pinch valve 28, illuminating the precursor by opening a shutter 144 mounted below the collimation adaptor, pumping the solutions again to wash out the cured microparticles 100 into a conical tube and also rebuilding the sculpted flows, and then repeating these steps multiple times. After a final cycle of process, the collection tube was centrifuged at 2,500 rpm for five (5) minutes to pull the microparticles 100 down to the bottom of tube. The supernatant is then removed and a rinse process is performed three times to get rid of residual precursor using DPBS with pluronic as surfactant. The rinse process included re-suspending the microparticles 100 in solution, centrifuging the microparticles 100 down toward the bottom of tube, pipetting out the supernatant gently to avoid generating flows and withdrawing carriers.

The dumbbell shaped microparticles 100 that are created exhibit self-aligning in the microfluidic channel 22. That is say, the microparticles 100 flow in the middle of the downstream microfluidic channel 22 and the large disc of the dumbbell (seen in FIGS. 4A and 5C) is located in the front or forward (i.e., downstream) direction with negligible tilting angle with respect to horizontal. Alignment of focusing of microparticles 100 in channels is important to optically interrogate them with a small focal area and with uniform conditions (e.g., downstream velocity, no rotation) for a camera or line-scan imaging modality.

After the formation of the microparticles 100, cell adhesive molecules are applied so that cells 136 can bind to the biotinylated region 160. During the photopolymerization process, biotin linkers are distributed across the surface of microparticle 100 at the biotinylated region 160. Streptavidin was is then incubated to bind to the biotinylated region 160, followed by the addition of a biotinylated biomolecule that is used to bind the cells 136. The biotinylated biomolecule may be chosen depending on the type of cell 136 that is desirous to be adhered to the microparticle 100. For example, certain cells (e.g., MDA breast cancer cells) may bind to collagen and biotinylated collagen may be used. FIG. 5A, for instance, illustrates a three-dimensional microparticle 100 that has a biotinylated region 160. Streptavidin is first added to bind to this biotinylated region 160. Finally, biotinylated collagen is added to form the final binding site for the addition of cells 136. For example, after formation and collection of the three dimensional microparticles 100, the surface is then prepped for cell adhesion.

As one example, MDA-MB-231 breast cancer cells were utilized to demonstrate the cell binding with microparticles 100, cell culture on the microparticles 100, and high speed imaging of cells 136 in flowing carriers. In this particular example, microparticles 100 were sequentially incubated in incubator 180 with 1 mg/mL streptavidin and then biotinylated collagen I overnight. After each incubation process, microparticles 100 were rinsed using DPBS solution with pluronic with volume many times larger than the volume of solution with microparticles 100. Dulbecco's Modified Eagle's medium (DMEM) solution with pluronic was then used to rinse the microparticles 100, transferring them into medium solution as illustrated in FIG. 5B. Microparticles 100 were first settled down on the bottom of an ultra-low attachment well (e.g., 96-well plate), and then 100 µL medium solution of suspending cells 136 with concentration of $4\times10^4$/mL was dispensed on the settled microparticles 100. In this embodiment, the cells 136 only adhered to one notch (i.e., top) of the protective region 130 of the microparticle 100 because cells 136 were seeded from the top. It should be understood that cells 136 may also be adhered to the other notch (i.e., bottom) of the protective region 130. In addition, while biotinylated collagen was used in this particular embodiment, it should be understood that any biomolecule or binding moiety (i.e., cellular binding moiety) can be used to selectively form a cell adherent area on the microparticle 100. This adherent zone or region on the microparticle 100 is preferably located within a protected region 130.

Figure 6A:
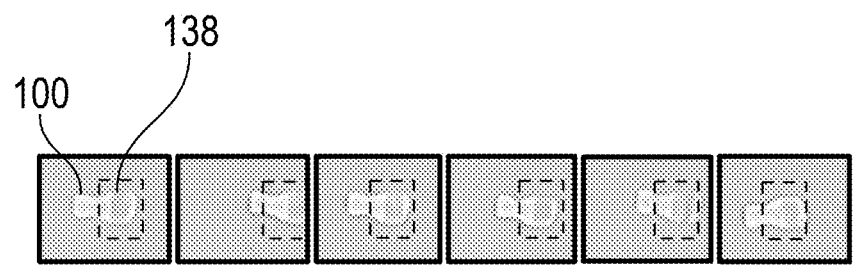
FIG. 6A illustrates brightfield microscope images of three dimsional microparticles having adherent cells lcoated in a protected region of the microparticle.
Figure 6B:
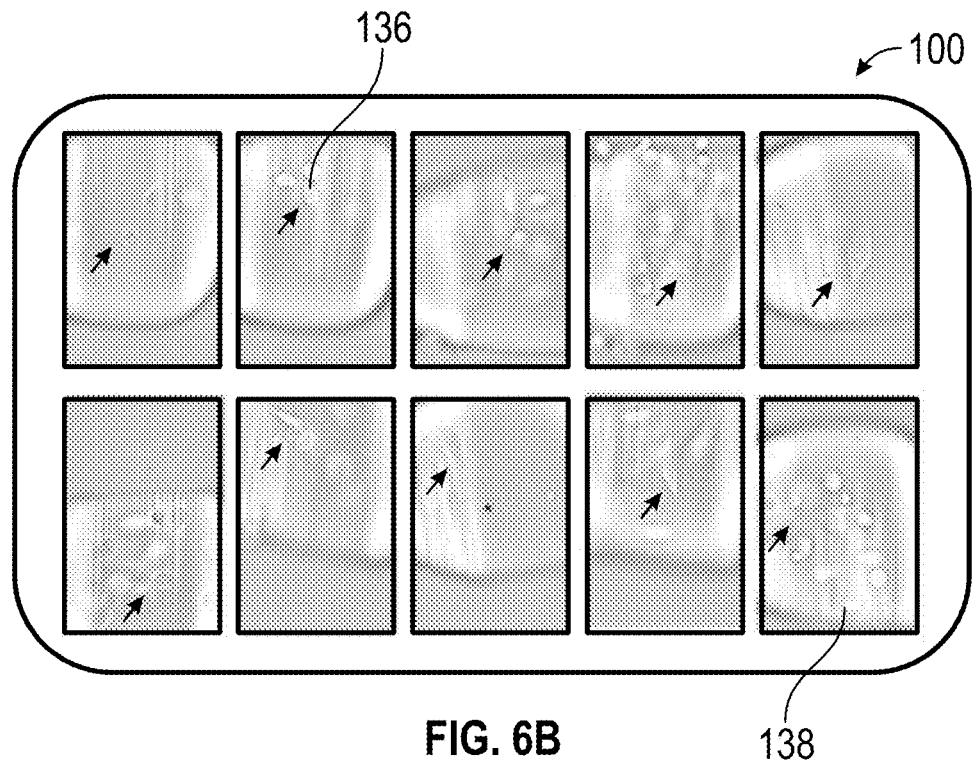
FIG. 6B illustrates magnified views of brightfield microscope images of three dimensional microparticles having adherent cells located in a protected region of the microparticle. Arrows point to cells that are adherent to the microparticles.

Experiments were also conducted whereby adherent-cells on the microparticles 100 were subject to flow cytometry and downstream imaging by injecting a medium where microparticles 100 with cells 136 adhered thereto were flowed into a straight microfluidic channel (150 µm×100 µm) followed by downstream imaging. Microparticles 100 with cells 136 adhered thereto were suspended in 500 µL medium. This solution was then pumped into the straight microfluidic channel with volume flow rate of 500 µL/min which corresponds to a Reynolds number of ~22. The microparticles 100 were then collected and maintained in an incubator for two days. Videos were recorded at a downstream region of the microfluidic channel using a high-speed camera 170 (FIG. 5C) and mercury light source with short exposure time. The videos were then analyzed for cells 136. FIG. 6A illustrates images obtained from the videos showing microparticles 100 with cells 136 adhered to the biotinylated region 160. FIG. 6B illustrates magnified or zoomed-in views showing the presence of cells 136 (see arrows) located within the protected region 130 of the microparticle 100. The images of microparticles 100 flowing in the microchannel demonstrate that the microparticles 100 consistently brought adherent cells 136 into a detection area with a narrower width of 300 µm and in the same focal plane. Moreover, the cells 136 were also examined for viability two (2) days after flowing through a microfluidic device. The microparticles 100 with adherent cells 136 were stained with calcein AM (green) to identify live cells 136 and ethidium bromide (red) to identify dead cells 136. The live/dead stain images showed that the cells 136 remain viable two (2) days after flow through experiment. Much of the structure of a cell 136 is visible while it adheres to extracellular matrix, enabling improved analysis and cell biology research based on such information rich features such as cytoskeletal structure, nuclear morphology, localization of mitochrondria, adhesive structures such as focal adhesions, epithelial cell polarization to apical and basal regions, formation of filopodia etc.

While the dumbbell shaped microparticle 100 was used to adhere cells 136, other shapes and configurations of the microparticle 100 are possible. For example, additional types of microparticles 100 were fabricated as seen in FIGS. 7A-7D. Their shapes were compared with the expected results from the computer-controlled inertial flow deformation system 14 (e.g., uFlow software system described herein). C/triangle microparticles were fabricated using aqueous photo-crosslinkable polymer PEGDA with Re~10, flow recycling time=5 s, and exposure time=1 s. Diamond/ellipsoid and nine other types of microparticles were made using organic solvent based UV optical adhesive (NOA89, Norland), pumped at Re~8 with flow recycling time=5 s, and exposure time=500 ms. To investigate the accuracy of uFlow, assuming all flow parameters including Re number are correctly proscribed, a systematic error in particle shape was defined as the difference between average dimensions of manufactured particles and uFlow predictions and random error as the difference between average and individual dimensions of a particle type experiment.

Figure 7A:
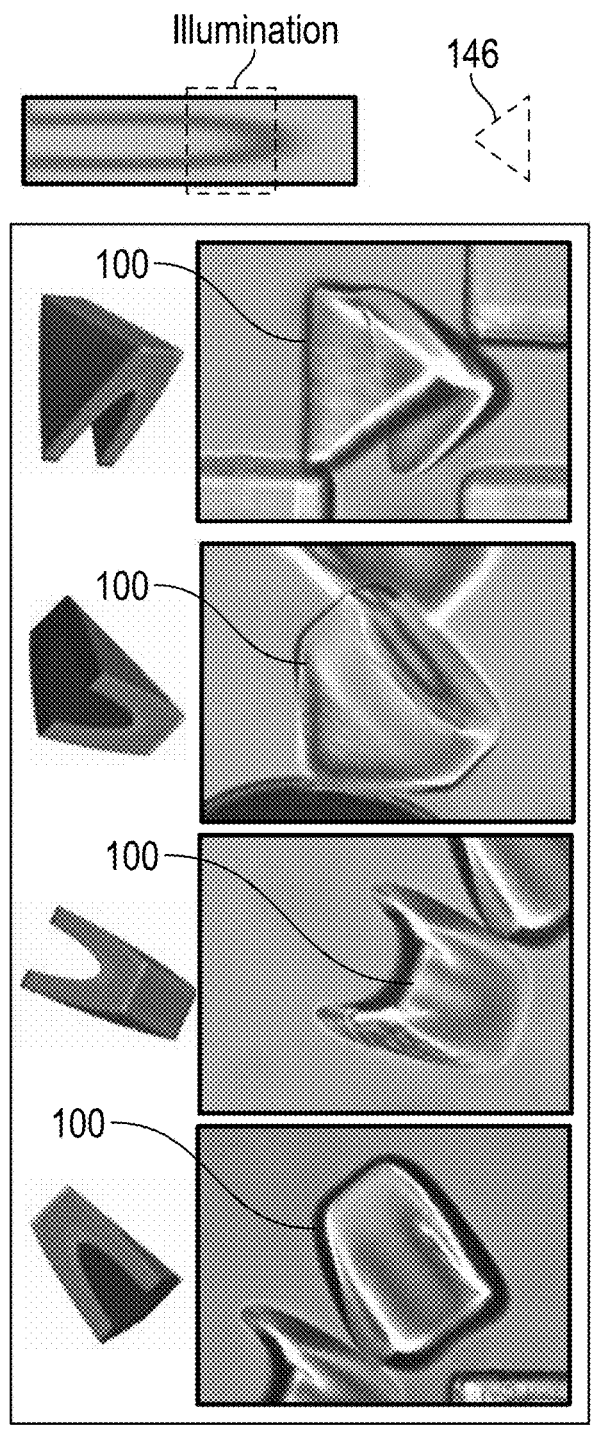
FIGS. 7A-7C illustrate various uFlow design predictions and fabricated microparticles. The predicted cross-sectional shape of the precursor stream is illustrated in cross-section, while the dashed rectangle represents the location of UV exposure for each design. The mask design is shown as a dashed contour. For each predicted three-dimensional shape the corresponding experimental shape was generated and is shown on the right hand side. All scale bars represent 100 µm.
Figure 7B:
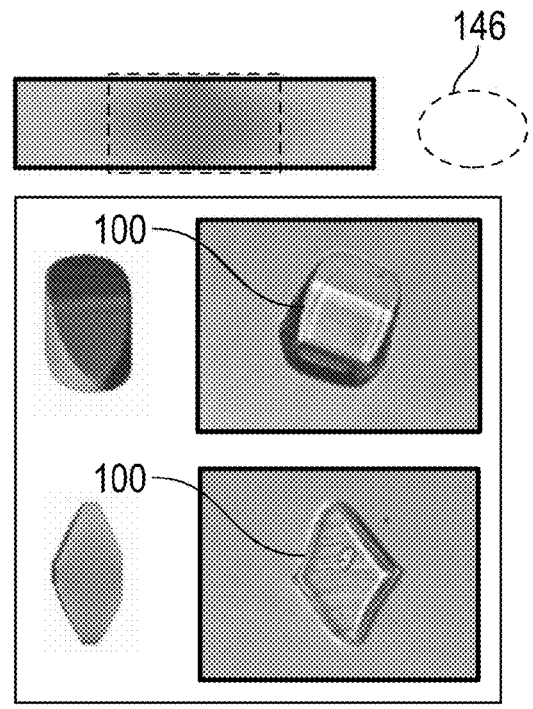
Figure 7C:
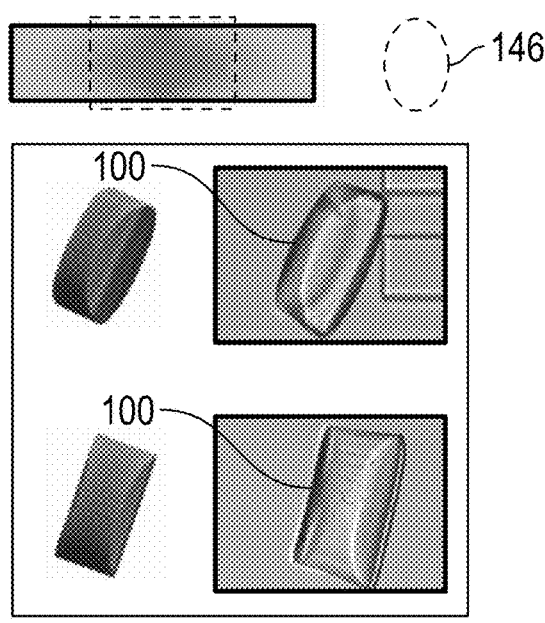
Figure 7D:
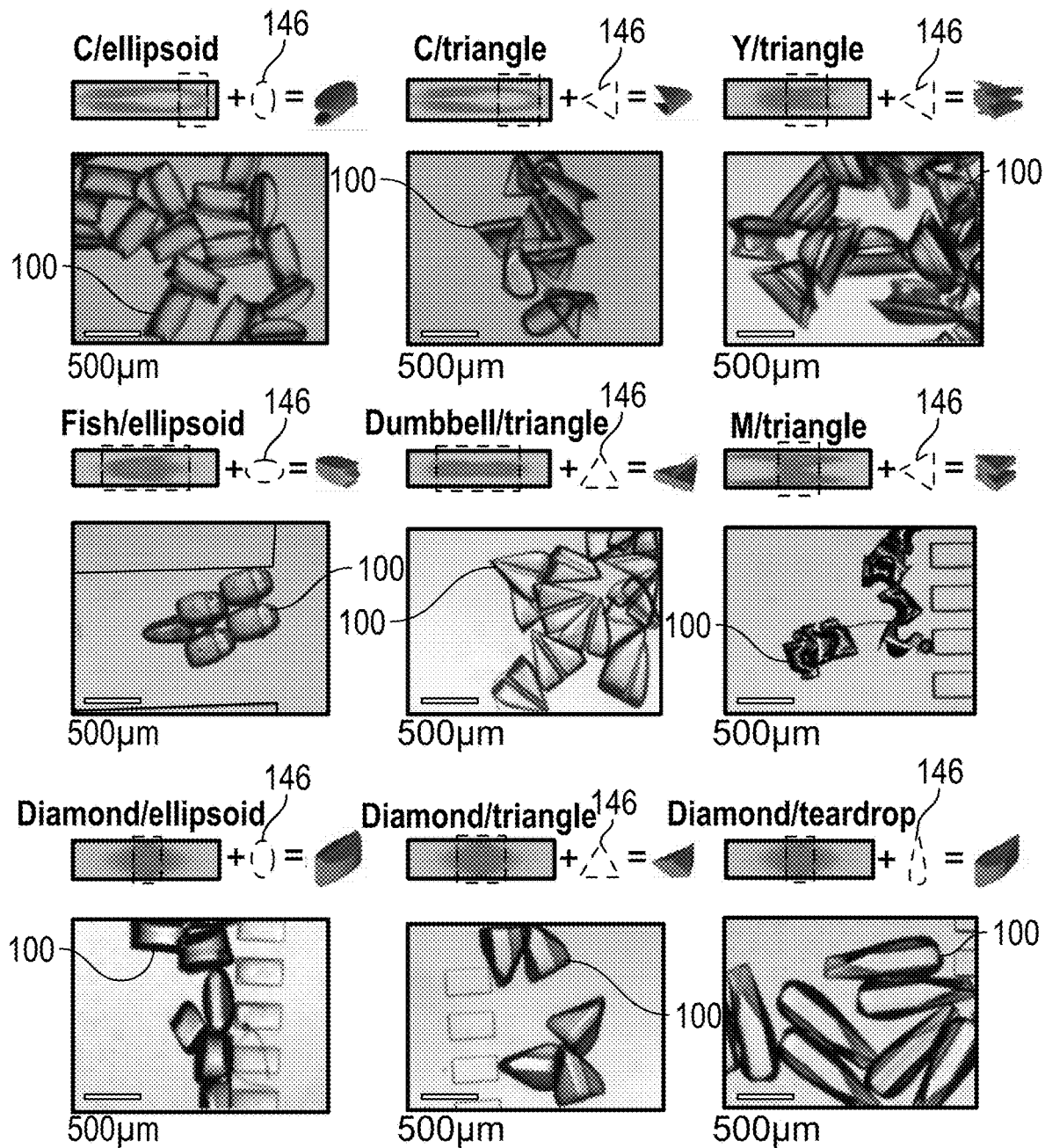
FIG. 7D illustrates additional three-dimensional shaped microparticles predicted using uFlow and fabricated using thiolene polymer. The three-dimensional shapes were selected for the purpose of intuitive illustration of the intersection of two extrusions. Six types of designs of the cross-sectional liquid mold shape were used including: C, Y, fish, dumbbell, M, and diamond shape. Three types of optical masks were also used: triangle, ellipsoid, and teardrop asymmetric shape (teardrop). The comparison between particle images (bottom) and computational predictions (top) show qualitative agreement in three dimensions and both directions of the extrusion. The fabrication results of shapes with liquid molds far from microchannel walls, for example, C, fish, dumbbell, and diamond shape, achieve higher quality production of the pattern. Asymmetry of the Y shape and slight loss of top or bottom regions of the M shape were observed likely due to the physical contact between microparticles and microfluidic channel walls.

Microparticles 100 fabricated using hydrogels (PEGDA) and UV optical adhesive (NOA89) possessed 3D shapes in qualitative and quantitative agreement with uFlow predictions (FIGS. 7A-7D). Photopolymerized PEGDA particles showed good qualitative agreement with uFlow predictions from multiple angles. Four images compare the uFlow prediction (left column in FIG. 7A) with the fabricated particle shape (right column in FIG. 7A) from different viewing angles. In this case the predicted liquid mold consisted of a curved void space and a particle with a qualitatively matching curved surface was replicated. To quantify the similarity between the predicted and fabricated particles the distance between two points at the tip of the "C" of these microparticles 100 were measured and agreed with predicted values with <1% systematic error on average. The repeatability of the fabrication system achieving <3% random error on average was also confirmed. Diamond/ellipsoid microparticles 100 fabricated using organic solvent based UV optical adhesive also agreed with predictions. Two orientations were shown in FIG. 7B (diamond) and FIG. 7C (ellipsoid) for each particle type, consisting of the ellipse major axis in a horizontal or vertical position. In the horizontal one, there was a systematic error of ~19% in distance across the diamond, in which fabricated microparticles 100 were always observed to have enlarged dimensions. Additional microparticle 100 types were fabricated with various combinations of liquid molds and UV patterns demonstrating the robustness, qualitative accuracy, and repeatability of fabrication as illustrated in FIG. 7D.

Figure 8A:
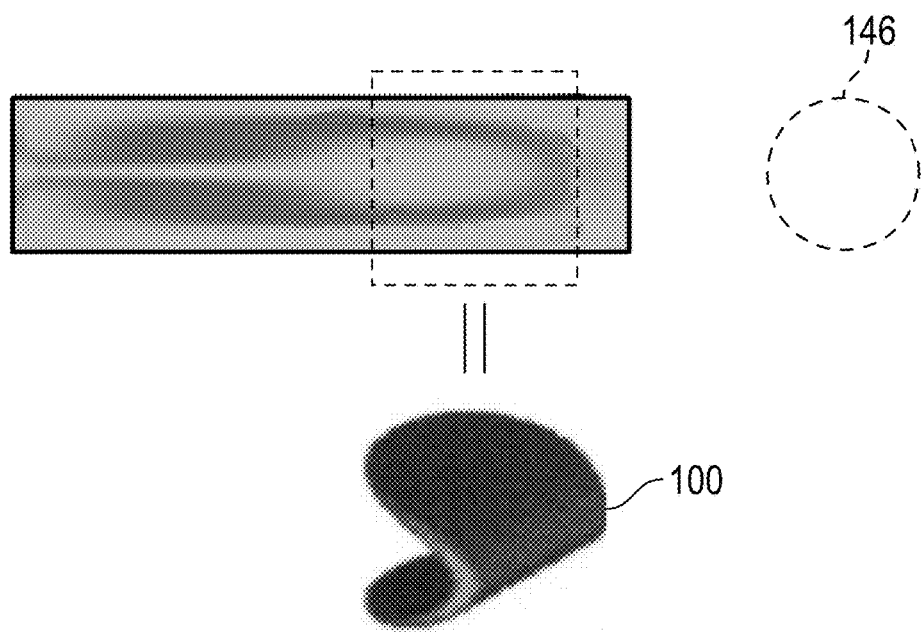
FIG. 8A a magnetic microparticle, shaped by the intersection of extrusions of a C-shaped flow and circle.
Figure 8B:
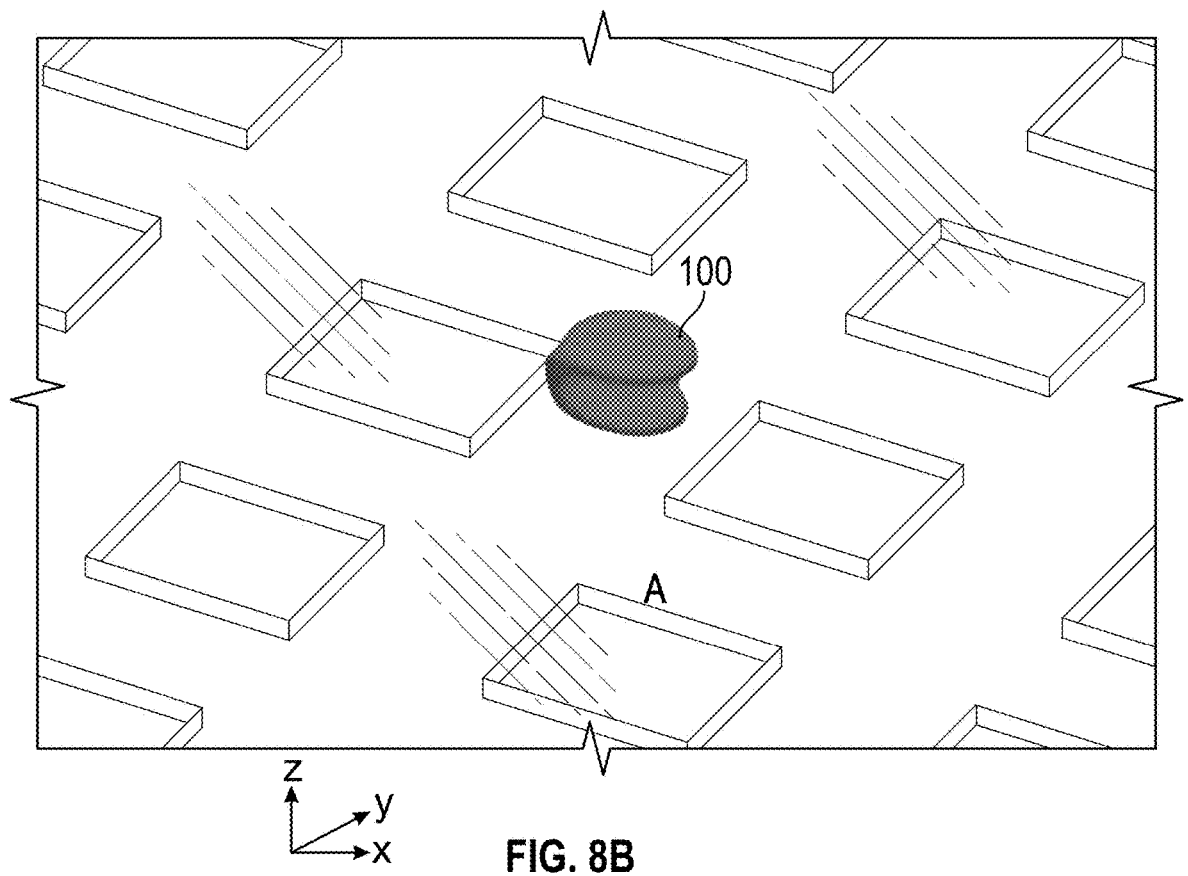
FIG. 8B illustrates the simulation domain of magnetic microparticles on a substrate with an array of micromagnetic elements.
Figure 8C:
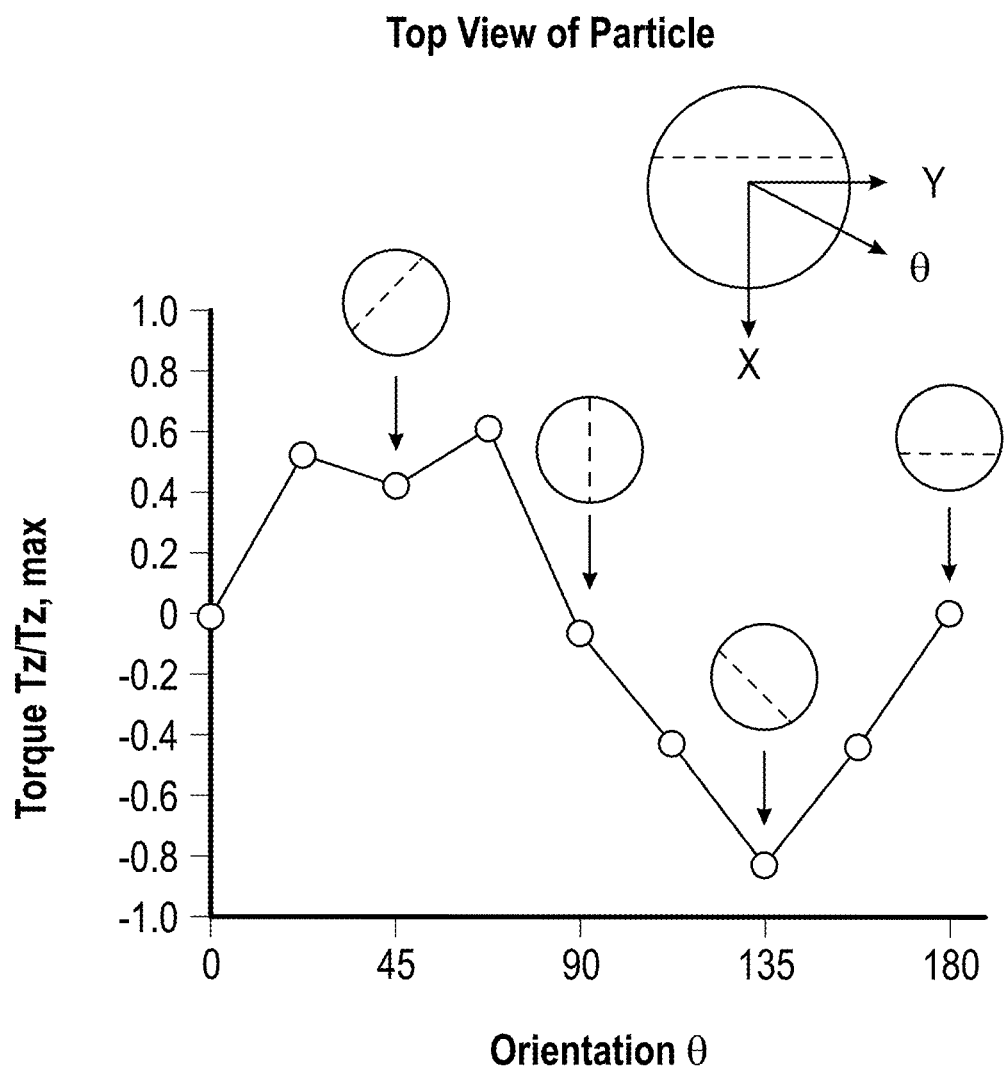
FIG. 8C illustrates the simulated torque applied on the microparticle versus the orientation identifies an equilibrium rotation at 90 degree.
Figure 8D:
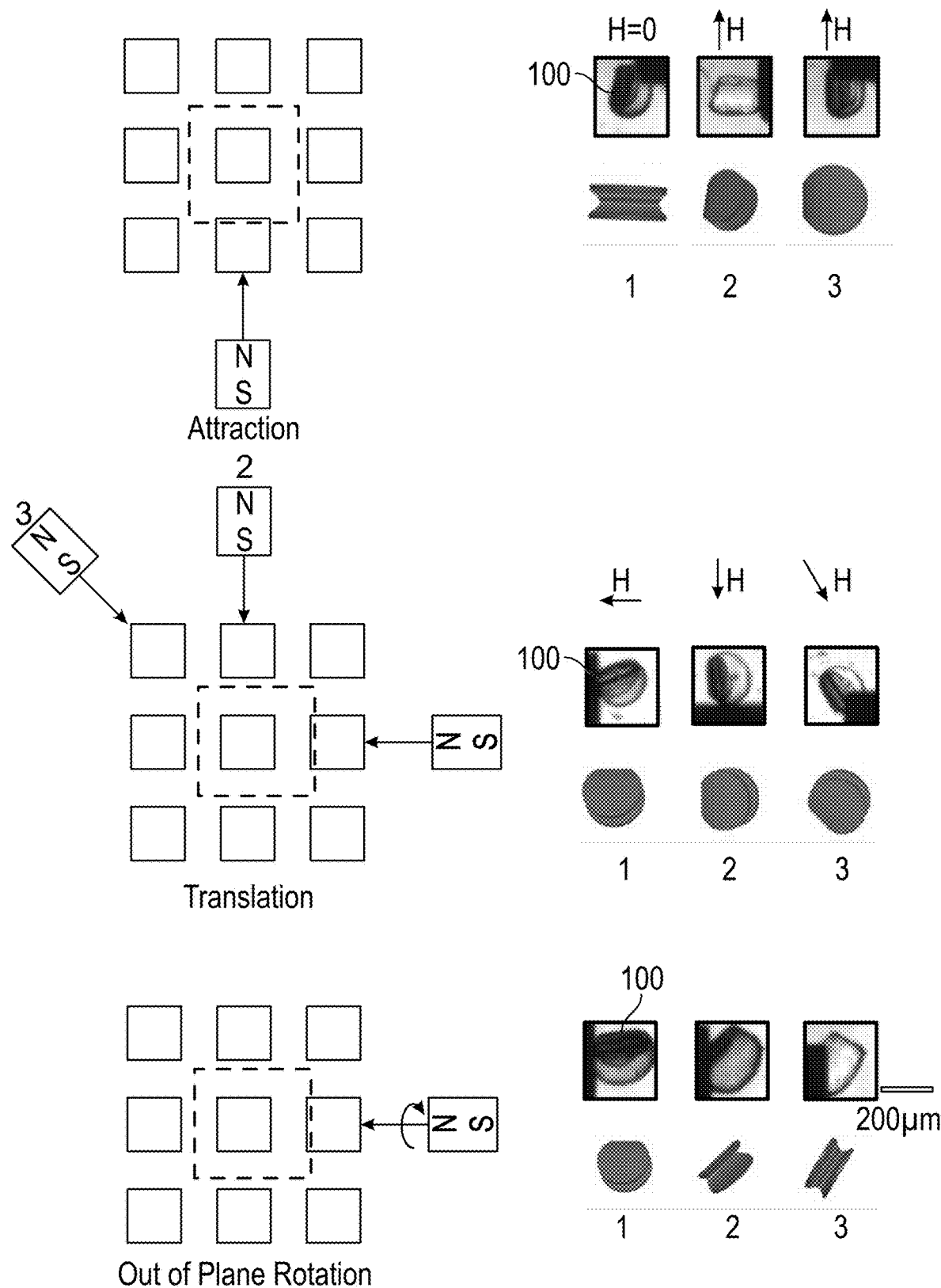
FIG. 8D illustrates sequential images for three types of motions of magnetic microparticles with a shifting external magnetic field: attraction, translation, and out of plane rotation. The left schematic represents the position of the permanent magnet in relation to the substrate. Three sequential images for each type show the initial, transient, and final position and orientation of the microparticle.

The fabrication system 10 was also used to fabricate magnetically anisotropic particles that could be oriented in 3D in an external magnetic field. C/circle magnetic microparticles 100 were designed using the computer-controlled inertial flow deformation system 14 (i.e., uFlow) as seen in FIG. 8A. The high transparency of the fabricated magnetic microparticles 100 without accumulation of clusters of magnetic nanoparticles indicated a homogenous distribution was achieved and magnetic properties could be considered uniform throughout the particle shape. However, because of the asymmetry in particle shape these microparticles 100 were expected to respond and orient to a preferred axis in response to an external magnetic field. These microparticles 100 were numerically and experimentally observed to align and oriented to arrays of magnetic gradient (and force) amplifying micromagnets. A microparticle 100 with the target orientation placed in between two micromagnetic elements using finite element method with COMSOL Multiphysics and following calculation of force integrated magnetic torque per unit area induced by the Maxwell stress tensor across the entire surface of the particle to arrive at the net torque applied on the microparticle 100 with each orientation. Simulation results show that the orientation of the magnetic microparticle 100 in the presence of a nearby micromagnet is stable at 90 degrees (and −90 degrees due to symmetry), where the opening of the particle faces to right (or left) (FIG. 8C). The magnetic microparticles 100 were randomly spread on the substrate (FIGS. 8B and 8D) and then an external magnetic field was applied to attract a microparticle 100 to the bottom edge of each magnetic element (seen in FIG. 8B). The attracted microparticles 100 were observed to be oriented with their open face to the right, agreeing with simulation. The attracted microparticles 100 could then be moved along the edges of the magnetic elements with a corresponding change in the external magnetic field direction in the 2D plane (FIG. 8D). Moreover, because of the magnetic anisotropy of the 3D shaped magnetic microparticle 100, shifting the magnetic field direction out of the 2D plane by rolling the external permanent magnet guided the attracted microparticles 100 to rotate out of plane in 3D, presenting an open face (FIG. 8D).

The ability to manufacture three-dimensional particles 100 with specific geometric shapes and features (including valleys, notches, grooves, holes or voids) is enabling for advanced biomaterials as well as materials with unique anisotropic mechanical, chemical, magnetic or optical properties. Three dimensional microparticles 100 with shape-dependent mechanical properties can be potentially applied as biosensors for the study of single cell mechanics while porous particles with selective adhesive regions within pores could serve as high surface area carriers for adherent cells in bioreactors while protecting the adhered cells from shear stresses accompanying transport of the cell carriers. Microparticles 100 in the hundred micrometer size range can self-assemble by applying external forces, e.g. capillary force, and designing interlocking shapes on the particles. For drug delivery and cell uptake, smaller particles can be produced by locally polymerizing the precursor stream, sheathing and engineering the precursor stream sequentially to reduce its size, or shrinking channel dimensions, which also has the benefit of enhancing viscous dissipation of momentum, although increasing the pressure to drive the flow. In addition, the anisotropic magnetic particles produced can be used for magnetically controlled inks, control of micro optic components, manipulation of microreactors or microcarriers with cells to be viewable, active sorting of microcarriers, and micro-actuators with soft structures.

The microparticles 100 that are generated that have adherent species bound thereto (e.g., cells 136, beads, markers, targets, or the like) can be subject to downstream analysis and detection. For example, the microparticles 100 may be flowed through a downstream microchannel and imaged using a high-speed camera such as that illustrated in FIG. 5C. Alternatively, or in combination, the microparticles 100 may be subject to optical excitation and fluorescent imaging and/or detection. For example, fluorescent species that are bound directly or indirectly to the microparticles 100 can be detected using a downstream fluorescent light detection system. The use of the microparticles 100 can be used to align the fluorescent species in a known location where they can be readily detected or imaged. Further, the fluorescent species may be protected from shear forces that may be generated within the microfluidic device 102.

While embodiments of the present invention have been shown and described, various modifications may be made without departing from the scope of the present invention. For example, features or aspects of one embodiment may be incorporated in other embodiments even if not specifically identified as being substitutable. The invention, therefore, should not be limited, except to the following claims, and their equivalents.

What is claimed is:

1. A method of forming three-dimensional shaped microparticles in a microfluidic device comprising:
    flowing a mixture of a monomer and photoinitiator in a microfluidic channel of the microfluidic device having a plurality of pillars disposed therein to define a flow stream having a pre-defined shape;
    temporarily stopping the flow stream;
    polymerizing one or more portions of the flow stream located downstream of the plurality of pillars by passing polymerizing light through one or more masks and onto the flow stream, the polymerization process forming a plurality of three-dimensional shaped microparticles;
    restarting the flow stream; and
    wherein the microfluidic device is coupled to a pump that pumps the mixture of the monomer and photoinitiator through the microfluidic device, the microfluidic device further including an output path and a valve disposed in the output path, wherein temporarily stopping the flow stream comprises automatically closing the valve and stopping the pump.

2. The method of claim 1, wherein the flow stream having the pre-defined shape is sculpted with a non-rectangular shape.

3. The method of claim 1, wherein the three-dimensional shaped microparticles comprise a protected region formed on each of the three-dimensional shaped microparticles.

4. The method of claim 3, further comprising adhering one or more cells to the protected region, wherein the mixture of monomer and photoinitiator further comprises a cellular binding moiety.

5. The method of claim 4, further comprising interrogating the three-dimensional shaped microparticles having the adhered one or more cells by imaging the three-dimensional shaped microparticles.

6. The method of claim 3, wherein the protected region comprises a notch.

7. The method of claim 3, wherein the protected region comprises one or more flexible regions.

8. The method of claim 3, wherein the protected region comprises a cell adherent region.

9. The method of claim 1, wherein the three-dimensional shaped microparticles comprise magnetic nanoparticles therein.

10. The method of claim 1, wherein the three-dimensional shaped microparticles have a barbell shape.

11. The method of claim 1, wherein the microparticles comprise a plurality of different materials in a layered configuration.

12. The method of claim 1, wherein the flow stream remains under high pressure as compared to atmospheric pressure in the microfluidic device while the flow stream is temporarily stopped.

13. The method of claim 1, wherein restarting the flow stream comprises opening the valve and turning on the pump.

14. The method of claim 1, wherein the one or more masks comprises a plurality of identically shaped masks in a linear arrangement interposed between the microfluidic device and a polymerizing light source.

15. The method of claim 1, wherein the three-dimensional shaped microparticles are less than 200 μm in their longest dimension.

16. The method of claim 1, wherein the mixture of a monomer and photoinitiator further comprises Biotin-PEG-acrylate.

* * * * *